US010593040B2

(12) United States Patent
Zouridakis

(10) Patent No.: US 10,593,040 B2
(45) Date of Patent: Mar. 17, 2020

(54) METHODS FOR SCREENING AND DIAGNOSING A SKIN CONDITION

(71) Applicant: University of Houston System, Houston, TX (US)

(72) Inventor: George Zouridakis, Houston, TX (US)

(73) Assignee: University of Houston System, Houston, TX (US)

(*) Notice: Subject to any disclaimer, the term of this patent is extended or adjusted under 35 U.S.C. 154(b) by 0 days.

(21) Appl. No.: 16/278,946

(22) Filed: Feb. 19, 2019

(65) Prior Publication Data
US 2019/0188851 A1 Jun. 20, 2019

Related U.S. Application Data

(63) Continuation of application No. 13/852,672, filed on Mar. 28, 2013, now abandoned.

(60) Provisional application No. 61/616,633, filed on Mar. 28, 2012.

(51) Int. Cl.
*H04N 9/47* (2006.01)
*H04N 7/18* (2006.01)
*G06T 7/00* (2017.01)
*A61B 5/00* (2006.01)

(52) U.S. Cl.
CPC .......... *G06T 7/0012* (2013.01); *A61B 5/0077* (2013.01); *A61B 5/444* (2013.01); *G06K 2209/05* (2013.01); *G06K 2209/053* (2013.01); *G06T 2207/10024* (2013.01); *G06T 2207/20081* (2013.01); *G06T 2207/30088* (2013.01)

(58) Field of Classification Search
CPC ...... G06K 2209/05; G06T 2207/10024; G06T 2207/20081; G06T 2207/30088; G06T 7/0012
USPC ............................................. 348/77; 382/110
See application file for complete search history.

(56) References Cited

U.S. PATENT DOCUMENTS

| | | | |
|---|---|---|---|
| 8,139,858 B1 | 3/2012 | Landwehr et al. | |
| 2004/0186351 A1* | 9/2004 | Imaizumi | A61B 1/00009 600/160 |
| 2004/0264749 A1 | 12/2004 | Skladnev et al. | |
| 2005/0273011 A1* | 12/2005 | Hattery | A61B 5/0059 600/476 |
| 2006/0257007 A1* | 11/2006 | Bartsch | G06F 19/321 382/128 |
| 2006/0269111 A1 | 11/2006 | Stoecker et al. | |
| 2008/0095429 A1* | 4/2008 | Wilensky | G06K 9/342 382/164 |
| 2008/0226151 A1* | 9/2008 | Zouridakis | A61B 5/0059 382/133 |

(Continued)

OTHER PUBLICATIONS

Yuan, Xiaojing, et al., "SVM-based texture classification and application to early melanoma detection." Engineering in Medicine and Biology Society, 2006. EMBS'06. 28th Annual International Conference of the IEEE. IEEE, 2006.

(Continued)

*Primary Examiner* — Fabio S Lima
(74) *Attorney, Agent, or Firm* — Carter, DeLuca & Farrell LLP; George Likourezos, Esq.

(57) ABSTRACT

Provided herein are digital-implemented methods for performing simultaneous analyses on an object on the skin of an animal body, for example, a human, to classify the object as a skin cancer, an ulcer or neither. The analyses are performed simultaneously on a hand-held imaging device.

13 Claims, 23 Drawing Sheets

(56) References Cited

U.S. PATENT DOCUMENTS

| | | |
|---|---|---|
| 2009/0028851 A1 | 1/2009 | Stuhmer et al. |
| 2009/0279760 A1 | 11/2009 | Bergman |
| 2010/0185064 A1* | 7/2010 | Bandic ................ A61B 5/0059 600/306 |
| 2012/0008838 A1* | 1/2012 | Guyon ................ G06T 7/0012 382/128 |
| 2013/0090571 A1* | 4/2013 | Nourani ................ A61B 5/103 600/587 |

OTHER PUBLICATIONS

Celebi, M. Emre, et al., "Lesion border detection in dermoscopy images." Computerized medical imaging and graphics 33.2 (2009): 148-153.

* cited by examiner

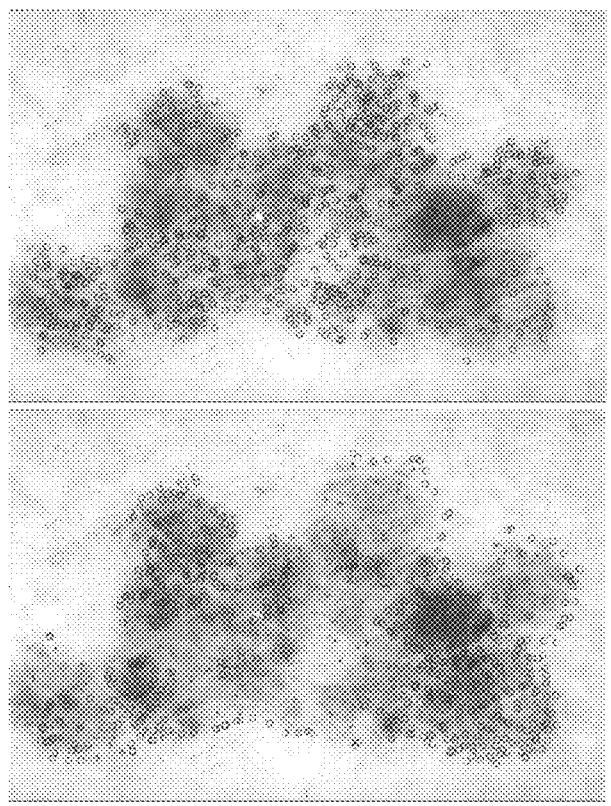
FIG. 1A
FIG. 1B
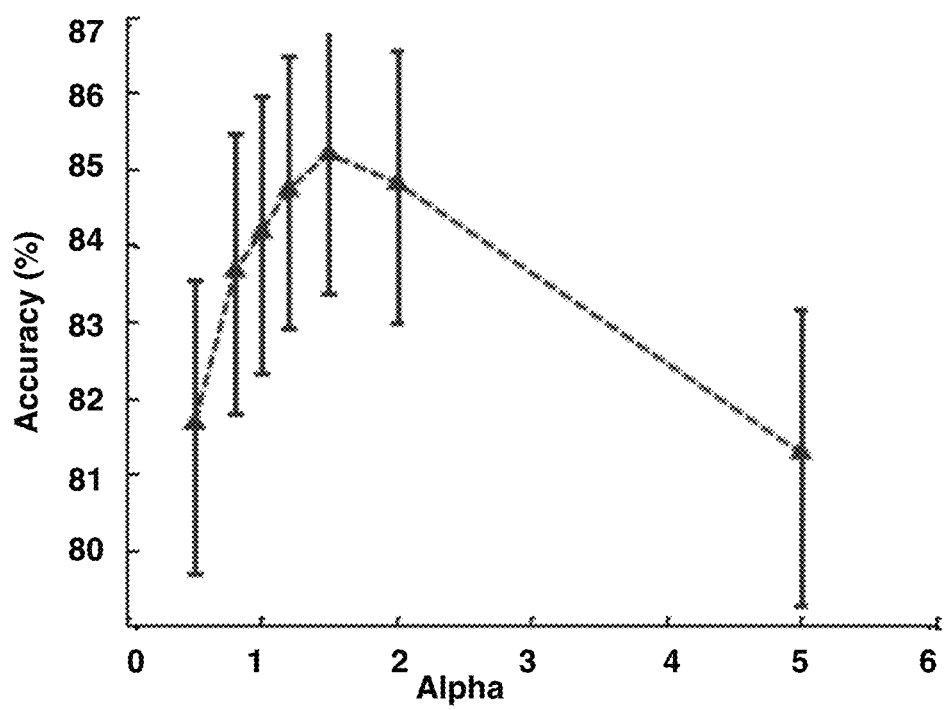
FIG. 1C

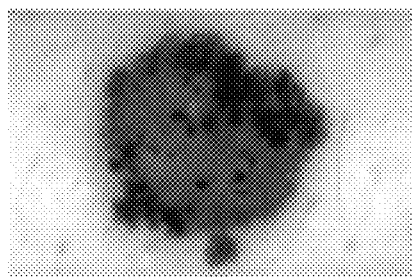
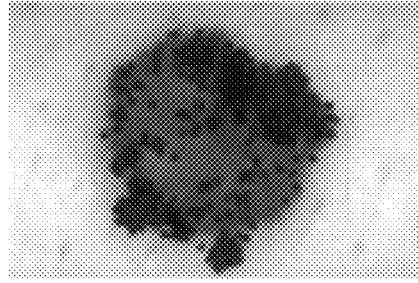
FIG. 2A  FIG. 2B
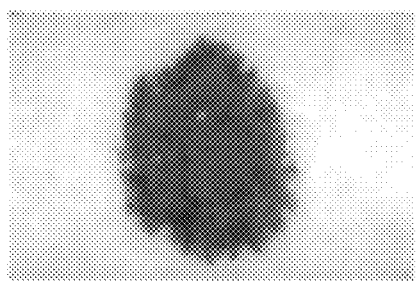
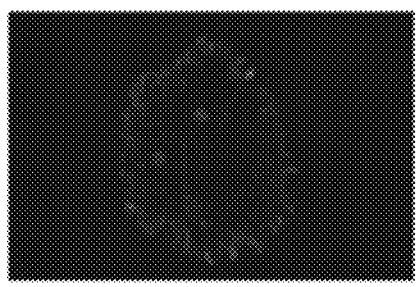
FIG. 3A  FIG. 3B
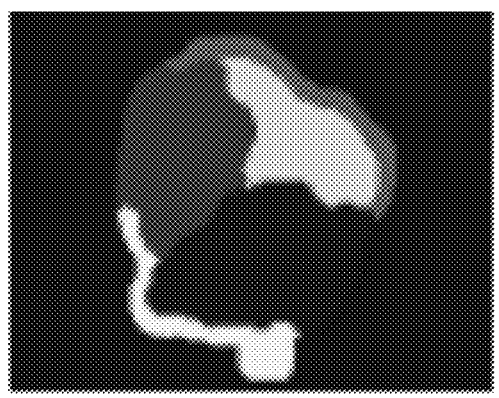
FIG. 4

METHODS FOR SCREENING AND DIAGNOSING A SKIN CONDITION

CROSS-REFERENCE TO RELATED APPLICATIONS

This is a continuation under 35 U.S.C. § 120 of pending non-provisional application U.S. Ser. No. 13/852,672, filed Mar. 28, 2013, which claims benefit of priority under 35 U.S.C. § 119(e) of provisional application U.S. Ser. No. 61/616,633, filed Mar. 28, 2012, now abandoned, the entirety of both of which are hereby incorporated by reference.

FEDERAL FUNDING LEGEND

This invention was made with governmental support under Grant Number IR21AR057921 awarded by the National Institutes of Health. The government has certain rights in the invention.

BACKGROUND OF THE INVENTION

Field of the Invention

The present invention relates to the fields of dermoscopy and software for the practice thereof on handheld biomedical screening devices. Specifically, the present invention provides a library of image processing and texture analysis algorithms that run on embedded devices for screening lesions and for plant diseases.

Description of the Related Art

The American Cancer Society predicts that there will be approximately 68,130 new cases of melanoma and 8,700 deaths because of melanoma in U.S. in 2010 (1). Thus, detection of an early melanoma is of paramount importance for successful skin cancer screening. The use of dermoscopy, an imaging technique to visualize structures inside pigmented skin lesions beyond the naked eye, and computerized systems for automated classification of dermoscopic images (2) can drastically improve the diagnostic accuracy of early melanoma. Image classification using interest points has shown success in previous studies (3).

In recent years, cellular phones have made the transition from simple dedicated telephony devices to being small, portable computers with the capability to perform complex, memory- and processor-intensive operations. These new smart devices, generally referred to as smartphones, provide the user with a wide array of communication and entertainment options that until recently required many independent devices. Given advances in medical imaging, smartphones provide an attractive vehicle for delivering image-based diagnostic services at a low cost.

As such, the new generation of smart handheld devices with sophisticated hardware and operating systems has provided a portable platform for running medical diagnostic software, such as the heart rate monitoring (4), diabetes monitoring (5), and experience sampling (6) applications, which combine the usefulness of medical diagnosis with the convenience of a handheld device. Their light operating systems, such as the Apple® iOS® and Google® Android®, the support for user friendly touch gestures, the availability of an SDK for fast application development, the rapid and regular improvements in hardware, and the availability of fast wireless networking over Wi-Fi and 3G make these devices ideal for medical applications.

Thus, there is a recognized need in the art for algorithms for improved detection, analysis and classification of skin lesions that can run on devices with limited memory and computational speed. More specifically, the prior art is deficient in image sampling, processing and texture analysis methods, algorithms and plug-in features, for detection and diagnosis of skin and ocular diseases and plant diseases, that are configured to operate on smart handheld devices. The present invention fulfills this long-standing need and desire in the art.

SUMMARY OF THE INVENTION

The present invention is directed to a portable imaging system. The portable imaging system comprises a hand-holdable imaging device having a digital camera, a display, a memory, a processor and a network connection and a library of algorithms tangibly stored in the memory and executable by the processor, where the algorithms are configured for identification of an object of interest present on a body. The present invention is directed a related portable imaging system further comprising algorithms tangibly stored and processor executable algorithms configured to display the object of interest and results of the classification thereof.

The present invention is directed to a method for identifying an object of interest present on a body. The method comprises acquiring an image of the object of interest on the body via the imaging device comprising the portable imaging system described herein and processing the acquired object image via the algorithms tangibly stored in the imaging device. The object in the image is identified based on patterns of features present in the imaged object, thereby identifying the object of interest on the body. The present invention is directed to a related method further comprising the step of displaying the results of image processing as each result occurs.

The present invention is directed further to a digital processor-implemented system for classifying an object of interest on an animal or plant body in real time. The system comprises a portable smart device comprising the processor, a memory and a network connection and modules tangibly stored in the memory. The modules comprise a module for segmentation of an imaged object, a module for feature extraction within the segmented object image and a module for classification of the object based on extracted features. The present invention is directed to a related digital processor-implemented system further comprising a module tangibly stored in the memory for display of the object of interest and results of the classification thereof.

The present invention is directed further still to a digital processor-implemented method for classifying an object of interest on an animal or plant body in real time. The method comprises the processor executable steps of digitally imaging the object of interest with the smart device comprising the digital processor-implemented system described herein, processing the digital image through the system modules and displaying the processed images and classification results on a display comprising the smart device. The modules comprise algorithms configured for segmenting the image based on saliency values to identify pixels thereof as comprising the imaged object or the background of the image to obtain an object boundary, extracting features from regions within the object boundary and comparing the extracted features to known object features in a support vector machine trained on the known features to obtain a classification of the object.

The present invention is directed further still to a digital processor-readable medium tangibly storing processor-executable instructions to perform the digital processor implemented method described herein.

The present invention is directed further still to a computer-readable medium tangibly storing a library of algorithms to classify an object of interest on a human or plant body. The algorithms comprises processor-executable instructions operable to obtain luminance and color components of the imaged object, classify pixels comprising the image as object pixels, if they belong to a common luminance and color foreground, as background pixels if they belong to a common luminance and color background or as remaining pixels, apply a classifier to the remaining pixels to classify them as object or foreground, calculate a saliency value for a plurality of patches within the segmented object and separate the patches into regions based on the saliency values, calculate an average intensity for the regions to identify them as a higher or as a lower intensity region, determine a sampling percentage for the two intensity regions, sample patches within the intensity regions by corresponding sampling percentages, extract one or more feature representations for the object, train a support vector machine (SVM) with known manually segmented objects, and classify the object based on the extracted feature representations inputted into the SVM.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and, therefore, are not to be considered limiting in their scope.

FIGS. 1A-1C depict segmentation examples based on saliency (FIG. 1A) and nonuniform (FIG. 1B) sampling and classification performance for different ratios of sampling densities between the informative and homogenous region (FIG. 1C). Blue circles represent patch centers in the more informative (darker) region, while red crosses correspond to patch centers in the less informative (more homogeneous) region.

FIGS. 2A-2B depict an original prior art image (7) (FIG. 2A) and interest points (FIG. 2B) detected by SIFT using a threshold adjusted to retain 0.25% of points in the lesion.

FIGS. 3A-3B depict an original prior art image (7) (FIG. 3A) and Frangi filtered image (FIG. 3B). Higher responses, i.e., brighter spots, are seen at curvilinear structures in the periphery of the lesion.

FIG. 4 depicts the segmentation inside the lesion in FIG. 2B.

FIG. 21A shows the effect of patch number and FIG. 21B shows the effect of patch size.

DETAILED DESCRIPTION OF THE INVENTION

Figure 5A:
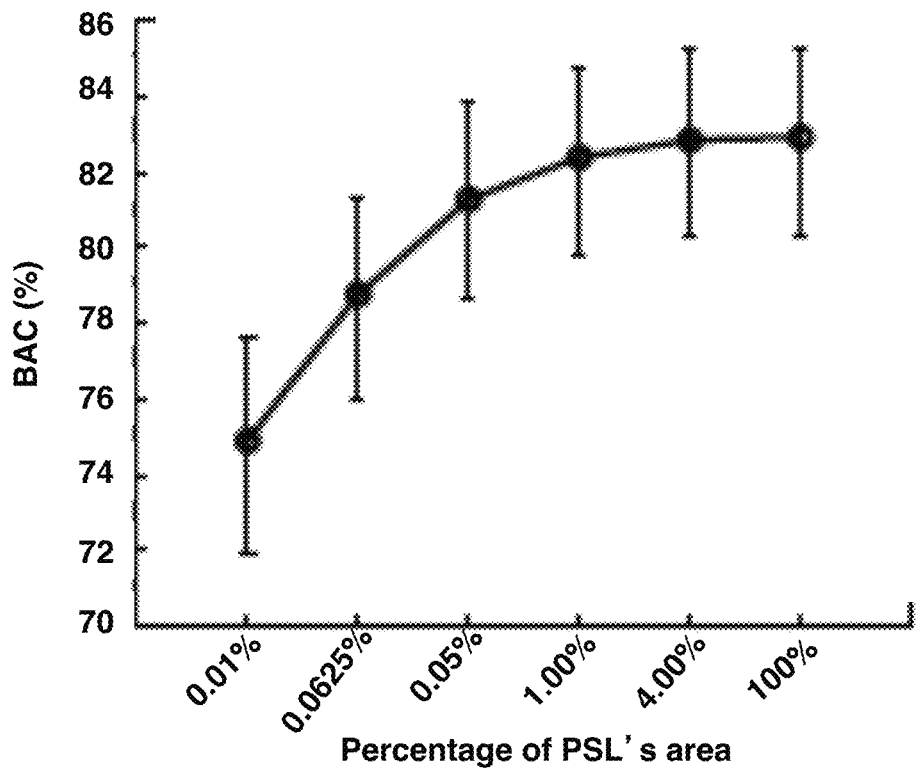
FIGS. 5A-5B illustrate the effect of the total points sampled on classification accuracy for balanced accuracy (BAC) (FIG. 5A) and area under the receiver operating characteristic curve (AUC) (FIG. 5B) for a pigmented skin lesion (PSL).

As used herein, the term "a" or "an", when used in conjunction with the term "comprising" in the claims and/or the specification, may refer to "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "body" and "subject" refer to a mammal, preferably human, or to a plant.

As used herein, the term "object" in reference to a body or a subject, refers to a lesion, wound, ulcer or other condition, or the skin or a region comprising the same that is located on the subject or body or refers to an area on the subject or body suspected of being or is malignant or associated with a disease or other pathophysiological condition.

In one embodiment of the present invention there is provided a portable imaging system, comprising a hand-holdable imaging device having a digital camera, a display, a memory, a processor and a network connection; and a library of algorithms tangibly stored in the memory and executable by the processor, said algorithms configured for identification of an object of interest present on a body. Further to this embodiment the portable imaging system comprises algorithms tangibly stored and processor executable algorithms configured to display the object of interest and results of the classification thereof.

In both embodiments the algorithms may comprise processor-executable instructions to segment the imaged object to detect a border of the object; extract features from the segmented object image; and classify the object based on the extracted features.

In an aspect of both embodiments the processor-executable instructions to segment the object may function to determine an initial contour of the imaged object; classify pixels as contained within the initial contour as foreground, as contained without the initial contour as background or as remaining pixels; and apply a classifier to the remaining pixels for classification as foreground or background.

In another aspect of both embodiments the processor-executable instructions to extract features may function to divide the segmented object image into regions based on saliency values calculated for at least one patch within the segmented object; divide the regions into two regions of higher or lower intensity based on average intensity values thereof; and extract feature representations from a sampling of patches within the intensity regions based on sampling percentages determined for the regions.

In yet another aspect of both embodiments the processor-executable instructions to classify the object may function to input the extracted feature representations into a support vector machine trained with manually segmented objects; and classify the object based on a comparison of the inputted extracted features with those in the trained support vector machine.

In all embodiments and aspects thereof the hand-held imaging device may be a smart device. Also, the body may be a human body or a plant body. In addition representative examples of the object of interest are a lesion, an ulcer, or a wound.

In another embodiment of the present invention there is provided a method for identifying an object of interest present on a body, comprising acquiring an image of the object of interest on the body via the imaging device comprising the portable imaging system described supra; processing the acquired object image via the algorithms tangibly stored in the imaging device; and identifying the object in the image based on patterns of features present in the imaged object, thereby identifying the object of interest on the body.

Further to this embodiment the method comprises displaying the results of image processing as each result occurs. In both embodiments identifying the object of interest occurs in real time. Also, in both embodiments the object of interest may be a melanoma or a Buruli ulcer.

In yet another embodiment of the present invention there is provided a digital processor-implemented system for classifying an object of interest on an animal or plant body in real time, comprising a portable smart device comprising the processor, a memory and a network connection; and modules tangibly stored in the memory comprising a module for segmentation of an imaged object; a module for feature extraction within the segmented object image; and a module for classification of the object based on extracted features. Further to this embodiment the digital processor-implemented system comprises a module tangibly stored in the memory for display of the object of interest and results of the classification thereof. Representative examples of the object may be a lesion, an ulcer or a wound.

In both embodiments the segmentation module comprises processor executable instructions to obtain luminance and color components of the imaged object; classify pixels comprising the image as object pixels, if they belong to a common luminance and color foreground, as background pixels if they belong to a common luminance and color background or as remaining pixels; and apply a classifier to the remaining pixels to classify them as object or foreground.

In an aspect of both embodiments the feature extraction module may comprise processor executable instructions to calculate a saliency value for a plurality of patches within the segmented object and separate the patches into regions based on the saliency values; calculate an average intensity for the regions to identify them as a higher or as a lower intensity region; determine a sampling percentage for the two intensity regions; sample patches within the intensity regions by corresponding sampling percentages; and extract one or more feature representations for the object. Also in both embodiments the classification module comprises processor executable instructions to train a support vector machine (SVM) with known manually segmented objects; and classify the object based on the extracted feature representations inputted into the SVM.

In another aspect the feature extraction module may comprise processor executable instructions to read input white light image as RGB and the segmentation result of the region; read input multispectral images in color channels and transform to gray scale; register multispectral images via maximization of mutual information with white light image as reference; extract feature representations within the ROI of multispectral images and within white light images; and select one or more relevant features from a pool of the extracted features.

In yet another aspect the feature extraction module may comprise processor executable instructions to read input white light image as RGB and the segmentation result of the region; read input multispectral images in color channels and transform to gray scale; register multispectral images via maximization of mutual information with white light image as reference; determine $V_{mel}$, $V_{blood}$, and $V_{oxy}$ for each ROI pixel to reconstruct maps of melanin, blood and oxygenating percentage; extract feature representations within the ROI from the reconstructed maps; and select one or more relevant features from a pool of the extracted features.

In yet another embodiment of the present invention there is provided a digital processor-implemented method for classifying an object of interest on an animal or plant body in real time, comprising the processor executable steps of digitally imaging the object of interest with the smart device comprising the digital processor-implemented system described supra; processing the digital image through the system modules, the modules comprising algorithms configured for segmenting the image based on saliency values to identify pixels thereof as comprising the imaged object or the background of the image to obtain an object boundary; extracting features from regions within the object boundary; and comparing the extracted features to known object features in a support vector machine trained on the known features to obtain a classification of the object; and displaying the processed images and classification results on a display comprising the smart device. In this embodiment the support vector machine may be trained on features comprising a melanoma or a Buruli ulcer.

In a related embodiment there is provided a digital processor-readable medium tangibly storing processor-executable instructions to perform the digital processor implemented method described herein.

In yet another embodiment of the present invention there is provided a computer-readable medium tangibly storing a library of algorithms to classify an object of interest on a human or plant body, said algorithms comprising processor-executable instructions operable to obtain luminance and color components of the imaged object; classify pixels comprising the image as object pixels, if they belong to a common luminance and color foreground, as background pixels if they belong to a common luminance and color background or as remaining pixels; apply a classifier to the remaining pixels to classify them as object or foreground; calculate a saliency value for a plurality of patches within the segmented object and separate the patches into regions based on the saliency values; calculate an average intensity for the regions to identify them as a higher or as a lower intensity region; determine a sampling percentage for the two intensity regions; sample patches within the intensity regions by corresponding sampling percentages; extract one or more feature representations for the object; train a support vector machine (SVM) with known manually segmented objects; and classify the object based on the extracted feature representations inputted into the SVM.

In one aspect the instructions to extract one or more feature representations for the object may calculate a saliency value for a plurality of patches within the segmented object and separate the patches into regions based on the saliency values; calculate an average intensity for the regions to identify them as a higher or as a lower intensity region; determine a sampling percentage for the intensity regions; sample patches within the intensity regions by corresponding sampling percentages; and extract the one or more feature representations for the object.

In another aspect the instructions to extract one or more feature representations for the object may read input white light image as RGB and the segmentation result of the region; read input multispectral images in color channels and transform to gray scale; register multispectral images via maximization of mutual information with white light image as reference; extract feature representations within the ROI of multispectral images and within white light images; and select one or more relevant features from a pool of the extracted features.

In yet another aspect the instructions to extract one or more feature representations for the object may read input white light image as RGB and the segmentation result of the region; read input multispectral images in color channels and transform to gray scale; register multispectral images via maximization of mutual information with white light image as reference; determine $V_{mel}$, $V_{blood}$, and $V_{oxy}$ for each ROI pixel to reconstruct maps of melanin, blood and oxygenating percentage; extract feature representations within the ROI from the reconstructed maps; and select one or more relevant features from a pool of the extracted features.

The present invention provides a library of algorithms, algorithm modules, plug-ins, and methods utilizable on a handheld portable imaging device, such as a smart device, for the identification and/or classification of an object of interest on a body. The library may be a C/C++ based library and may be downloaded and accessed as a plug-in or stored in the memory on a handheld smart device. Representative examples of such smart devices are, but not limited to, Apple® iOS®-based devices, such as iPhone®, iPad® and iPod Touch®, which are trademarks of Apple Inc., registered in the U.S. and other countries, and Android®-based devices, which is a registered trademark of Google Inc. The library comprises algorithms useful for the processing, texture analysis and classification of an image of an object of interest on a human or plant body skin lesion as malignant or benign. The algorithms are generally applicable to segmentation, feature extraction and classification of the object. For example, the object of interest may be identified or classified as a benign or malignant lesion, an ulcer, for example, but not limited to, a Buruli ulcer, or a wound.

Thus, provided herein are methods, particularly, digital processor-implemented methods for identifying or classifying the object of interest via the algorithms or modules comprising the same. The method utilizes the algorithmic library implemented on a handheld smart device, for example, a smartphone, as described herein. An image is acquired with the smartphone. Image acquisition optionally may utilize an external attachment that can provide illumination and magnification. The library of algorithms or modules is implemented on the smart device to operate on the image and a classification score is obtained, as described. As such cancers and other diseases of a human or plant body may be diagnosed. Particularly, the method enables diagnosis of a skin cancer, such as melanoma, or a skin disease, such as Buruli ulcer. A sufficient resolution enables the detection of and distinction among other types of lesions, ulcers or wounds. Moreover, the algorithms are configured to enable to run a Buruli analysis and a skin lesion analysis at the same time. The algorithms provided herein also are configured to process multispectrally-acquired images or optical images obtained with lights of different frequencies utilizing feature extraction and classification algorithms.

The present invention also includes a digital processor-readable or computer-readable medium that can tangibly store the algorithms and/or the processor-executable instructions or methods contained therein. Such readable media are well-known and standard in the art and can comprise a memory, such as on the smart device or other networked computer or a diskette, memory stick or flash drive from which the algorithms can be downloaded to the smart device, for example as a plug-in.

Moreover, the present invention provides an automated portable system for identification or classification of the object of interest. The system comprises a smart handheld device having an operating system, memory, processor, display screen, and lens and means for image acquisition, such as a digital camera, and is networkable, as is well-known and standard in the art. The system is configured to acquire and display an image of the object and to operate the library/modules of algorithms on the acquired image to process, identify patterns of object features, and classify the object. While the system is configured to operate on the smart handheld device, the device can wirelessly port the information or results to another smart device or desktop computer by methods well-known in the art.

It is contemplated that the library of algorithms provided herein may be utilized to detect ocular diseases, such as glaucoma. With an imaging technology suitable to allow visualization of the retinal tissue at an adequate resolution, the library of algorithms provided herein may be utilized for automatic analysis of the acquired image noninvasively in real time. Moreover, a handheld smart device comprising the library may be useful in obtaining and analyzing in real time infrared images of leaves to detect plant diseases or insect infestations or fungal infections in good time to save the crop. This results in successful agricultural management and improved crop productivity.

The following examples are given for the purpose of illustrating various embodiments of the invention and are not meant to limit the present invention in any fashion.

EXAMPLE 1

Methods

An image, such as skin lesion, can be acquired using a smartphone camera, with or without an external attachment that can provide illumination and magnification, or can be loaded from the photo library to provide the diagnosis in real time. The application can process images taken either with the iPhone® camera or taken with an external camera and uploaded to the image library on the phone. To test the application, images from a large commercial library of skin cancer images that were annotated by dermatologists (7) are uploaded to the phone. Intra-observer and inter-observer agreement could be low for certain criteria (8). All images were segmented manually to provide an evaluative level against which the automated techniques of the applications presented herein were compared. Prior to processing, if necessary, the images are converted from color to 256 level greyscale.

The iPhone 4® is a smartphone developed by Apple Inc., and features an Apple® A4 ARM® processor running at 1 GHz, 512 MB DDR SDRAM (Advanced RISC Machines, Ltd), up to 32 GB of solid state memory, a 5 MPixel built-in camera with LED flash, and 3G/Wi-Fi/Bluetooth® (Bluetooth SIG) communication networks. Thus, it has all the features, computational power, and memory needed to run the complete image acquisition and analysis procedure in quasi real time. There is lot of potential for such a device in medical applications, because of its low cost, portability, ease of use, and ubiquitous connectivity.

7-Point Checklist Criteria for Diagnosis of Melanoma

The 7-point checklist includes seven dermoscopic features that can be detected with high sensitivity and decent specificity by even less experienced clinicians. The seven points of the list are subdivided into three major and four minor criteria, reflecting their importance in defining a melanoma. To score a lesion, the presence of a major criterion is given two points and that of a minor one point. If the total score is greater than or equal to 3, the lesion is classified as melanoma.

The major criteria are: 1) Atypical pigment network: Black, brown, or gray network with irregular meshes and thick lines; 2) Blue-whitish veil: Confluent gray-blue to whitish-blue diffuse pigmentation associated with pigment network alterations, dots/globules and/or streaks; and 3) Atypical vascular pattern: Linear irregular or dotted vessels not clearly combined with regression structures and associated with pigment network alterations, dots/globules and/or streaks.

The minor criteria are 1) Irregular streaks: Irregular more or less confluent, linear structures not clearly combined with pigment network lines; 2) Irregular pigmentation: Black, brown, and/or gray pigment areas with irregular shape and/or distribution; 3) Irregular dots/globules: Black, brown, and/or gray round to oval, variously sized structures irregularly distributed; 4) Regression structures: Associated white scar-like and gray blue, peppering, multiple blue gray dots.

EXAMPLE 2

Non-Uniform Sampling for Bag-of-Features Classification

Dataset

A dataset with 645 epiluminescence microscopy (ELM) images, in which 491 lesions are benign and 154 lesions are melanoma, was used. The images are mainly collected from a commercial database (7). The total image size ranges from 712×454 to 1,024×768 pixels, while the lesion size ranges from 7,662 to 804,527 pixels.

Procedure

For bag-of-features-based classification, first, patches are extracted from every lesion, and then, for each patch, patch descriptors are generated using color moments and Haar wavelet coefficients, which capture the color and texture information. Then, each patch is assigned to a codeword from a pre-learned codebook, using hard assignment, as described herein. After that, a final feature vector is generated by pooling the assignments of all patches extracted from the lesion. For the classifier, support vector machines (SVMs) with a $\chi^2$ kernel are used, which currently represent state-of-art settings for a bag-of-features model.

Ten times ten-fold stratified cross-validation was performed to evaluate the performance of the method. Performance criteria include sensitivity, specificity, balanced accuracy (BAC, i.e., average of sensitivity and specificity), and area under the receiver operating characteristic curve (AUC). For sensitivity and specificity, both the mean and 95% confidence interval estimated from a binomial distribution are reported, and the average for BAC. Similarly, for AUC both the mean value and the standard deviation obtained are shown.

Occurrence-based Contextual Saliency

The saliency measure $S_i^o$ uses co-occurrence information between patches and codewords in images. Given a patch $x_i$, saliency is defined as the average likelihood of the image patches, $$S_i^o = \frac{1}{n}\sum_{j=1}^{n} \varphi(x_j|x_i). \quad \text{(Eq. 1)}$$

Here, $\varphi(x_j|x_i)$ can be interpreted as a compatibility score between $x_i$ and $x_j$. That is, if patch $x_i$ has been seen in an image, a higher score for patch $x_j$ means that it will appear in the same image with a higher probability. The function $\varphi(x_j|x_i)$ can be computed in the following steps.

Let $x_i$ and $y_i$ denote a patch and the corresponding patch descriptor, respectively. Then each image patch $x_i$ is assigned to a codeword $w_a$ in the codebook. These assignments may be soft or hard, and the probability of patch being assigned to codeword is given by $$\alpha_{ia} = p(w_a|y_i) \quad \text{(Eq. 2)}.$$

The value $w_a$ is discrete, while the values of $\alpha_{ia}$ for all codewords sum to one, i.e., $$\Sigma_{a=1}^{m} p(w_a|y_i)=1.$$

The value of $\varphi(x_j|x_i)$ is computed by marginalizing over all possible codeword assignment for $x_j$.

$$\varphi(x_j|x_i) = \sum_{b=1}^{m} p(w_b|y_j)\varphi(w_b|x_i), \quad \text{(Eq. 3)}$$

where $\varphi(w_b|x_i)$ is the compatibility score between $w_b$ and $x_i$. In the same way, $\varphi(w_b|x_i)$ can be obtained by marginalizing over all possible codeword assignment for $x_i$ $$\varphi(w_b|x_i) = \sum_{a=1}^{m} p(w_a|y_i)p(w_b|w_a). \quad \text{(Eq. 4)}$$

By rearranging Equation 1, Equation 3, and Equation 4, Eq. 5 was obtained $$S_i^o = \frac{1}{n}\sum_{j=1}^{n}\sum_{a=1}^{m}\sum_{b=1}^{m} p(w_a|y_i)p(w_b|y_j)p(w_b|w_a). \quad \text{(Eq. 5)}$$

where n is the number of pixels, m is the number of clusters, $$p(w_a|y_i) = \begin{cases} 1 & \text{if } y_i \subset w_a \\ 0 & \text{otherwise} \end{cases} \quad \text{(Eq. 6)}$$

$$p(w_b|y_j) = \begin{cases} 1 & \text{if } y_j \subset w_b \\ 0 & \text{otherwise} \end{cases} \quad \text{(Eq. 7)}$$

where $p(w_b|w_a)$ is the empirical conditional probability of observing codeword $w_b$ given that codeword $w_a$ has been observed somewhere in the image. These can be learned through Maximum Likelihood Estimator (MLE) counts from the training images.

Since saliency measures how well an individual patch can predict the occurrence of other patches in the same image, pixels with higher saliency values always belong to the relatively more homogenous background region. Therefore, some informative patches with lower saliency values are missed when using saliency-based image sampling.

Nonuniform Sampling Strategy

The basic idea of nonuniform sampling is to sample more patches from dermoscopically interesting regions, which are obtained by segmentation according to patch saliency and pixel intensity. It consists in four main steps:
1. Calculate saliency values for all patches;
2. Separate the lesion into two regions based on saliency;
3. Choose informative and homogeneous regions according to pixel intensities;
4. Decide sampling densities for the two separate regions.

In Step 1, saliency values are calculated using Equation 3 for each patch, and then k-means clustering is applied to separate the lesion into two regions. Subsequently, the region with lower pixel intensities was chosen as the informative region, and the other region as the homogenous one. That is because with pigmented skin lesions, dermatologists always pay more attention to the dark areas of a lesion to diagnose a melanoma. Then the sampling density for each region was chosen. When random sampling is applied to these two distinct regions, more patches are extracted from the informative region and fewer from homogeneous one. The sampling densities are controlled by the following equation, $$P_i = (\alpha \cdot A_i/\alpha \cdot A_i + A_h) \times 100\% \quad \text{(Eq. 8)}$$

where $P_i$ represents the percentage of patches sampled from the informative region, and $A_i$ and $A_h$ are the areas of the informative and homogeneous regions, respectively. The ratio of sampling densities of informative to homogeneous region is $\alpha$.

The coefficient $\alpha$ can be fixed or be allowed to vary dynamically. A dynamic $\alpha$ can be obtained by considering the saliency values of the two regions, which means that a big difference in saliency will result in a big difference in sampling density between two regions. FIGS. 1A-1B shows examples of saliency-based sampling and nonuniform sampling. It is obvious that saliency-based sampling incorrectly captures more information from the homogeneous background and misses informative patches that it considers as nonsalient. In contrast, the proposed nonuniform method correctly emphasizes the region that contains more DIPs.

Comparison of Sampling Strategies

The instant method is compared against plain saliency-based sampling (8), whereby patches with higher saliency values are considered of higher importance. To avoid the influence of the number of patches extracted and of the patch size, for both sampling strategies the patch size was fixed to 24×24 pixels and the patch percentage to approximately 4%. Table 1 shows the resulting classification performance for the two approaches. It can be seen that the proposed method achieves better accuracy than saliency based sampling. That is because patches with higher saliency values always belong to the relatively more homogenous region of the lesion, while the most informative patches from the skin lesion that are less frequent, and thus have lower saliency values, are missed. On the other hand, the method uses saliency as a measure to separate the image into more informative and less informative regions, while pixel intensities are used to identify the informative one. In this way, when analyzing pigmented skin lesions, more patches are sampled from the informative region that contains more DIPs.

TABLE 1

Classification performance using different sampling strategies

| Methods | Sensitivity (95% CI) | Specificity (95% CI) | BAC (95% CI) | AUC (std) |
|---|---|---|---|---|
| Saliency | 89.53 [86.91, 91.79] | 84.45 [85.73, 90.81] | 88.99 [86.32, 91.30] | 96.78 ± 2.12 |
| Nonuniform | 93.67 [91.50, 95.42] | 92.00 [89.63, 93.97] | 92.83 [90.57, 94.70] | 98.69 ± 1.12 |

Effects of Saliency

To demonstrate the benefits of using saliency for lesion sampling, as a control another sampling method was added, which both segments an image and chooses the informative region based on pixel intensity. Again, patches of size 24×24 pixels covering 4% of the total lesion area are sampled with this method, and random sampling is applied in the separate regions. Table 2 shows the resulting classification performance for the two approaches. It can be seen that lesion separation according to patch saliency can achieve a better classification performance than separation based only on pixel intensity. Thus, saliency provides an effective way to separate a lesion into informative and homogeneous regions.

TABLE 2

Classification performance using different sampling strategies

| Methods | Sensitivity (95% CI) | Specificity (95% CI) | BAC (95% CI) | AUC (std) |
|---|---|---|---|---|
| Intensity | 88.67 [85.96, 91.01] | 86.49 [83.61, 89.03] | 87.58 [84.79, 90.02] | 95.89 ± 2.45 |
| Nonuniform | 93.67 [91.50, 95.42] | 92.00 [89.63, 93.97] | 92.83 [90.57, 94.70] | 98.69 ± 1.12 |

Effects of Sampling Density

The ratio of sampling densities between informative and homogeneous regions can also affect classification accuracy. For the nonuniform sampling method, different values for the coefficient α in Equation 4 were tested, which represent different ratios of sampling densities whose influence is shown in FIG. 1C. When α equals one, nonuniform sampling is equivalent to uniform sampling. As α increases above one, and more patches are sampled from the informative region, the classification accuracy also increases. However, when α becomes too large, the overall performance decreases as well. This suggests that there is a minimum amount of complementary information provided by the homogeneous region that is essential for accurate classification. In summary, patches from informative regions that contain more dermoscopically interesting features should be sampled more densely, but patches from homogeneous regions which provide complementary information should not be ignored. The best performance can be achieved when α lies within (1, 2).

EXAMPLE 3

Evaluation of Sampling Strategies of Dermoscopic Interest Points (DIPs) in Melanomas
Dataset A dataset with 1,505 epiluminescence microscopy (ELM) images, in which 1,098 lesions are benign and 407 lesions are melanoma were used. The image size ranges from 712×454 to 1,024×768 pixels, and lesion size ranges from 7,662 to 804,527 pixels. Manual segmentation of all lesions is used to ensure that evaluation of the various sampling strategies is not affected by possible differences in automated identification of the lesion boundary.
Procedure The lesion classification procedure (9) consists of five main steps: image sampling, feature extraction, coding, pooling, and final classification (10). For a given image, identify DIPs inside the lesion are identified first and then a patch is extracted around each DIP. On each patch, several low level texture and color features were computed using Haar wavelets and color moments, which are important for melanoma detection. In the coding stage, a patch is assigned to a codeword from a pre-learned codebook using hard or soft assignment. Herein, each patch is assigned to its nearest neighbor in the codebook with hard assignment. The assignments of all patches extracted from a lesion are pooled into one feature vector. The last step is to classify the lesion based on the feature vector obtained from pooling.

Ten times ten-fold stratified cross-validation is performed using sensitivity, specificity, balanced accuracy (BAC, i.e., average of sensitivity and specificity), and area under the receiver operating characteristic curve (AUC) as performance criteria. For sensitivity and specificity, the mean and 95% confidence interval (CI) estimated from a binomial distribution are reported, and their average for BAC. For AUC both the mean value and standard deviation (std) of the values obtained are shown.
Image Sampling Strategies The sampling operator selects N pixels inside a lesion and then it centers a p×p pixel patch at each pixel location. For DIP detection, four sampling strategies are investigated. The first two are specifically designed for blobs and curvilinear components, respectively, which are the typical structures seen inside a lesion (11). The other two, however, are not targeting any particular lesion structure; yet, they result in excellent image classification performance.

Detector for blobs and corners: Blobs, dots, and globular structures are frequently observed in a lesion. The scale-invariant feature transform (SIFT) (12) is used to detect these structures, a procedure also used in (11) (FIGS. 2A-2B).

Detector for curvilinear structures: the SIFT operator is not stable for ridge detection (12) and it may fail to localize curvilinear structures in the lesion, as it was noted also by Zhou et al (11). Instead, for curvilinear structures, a Frangi filter (Frangi) is applied at three scales σ=1, 2, and 3 (10). Points with higher filter responses have higher probabilities of being curvilinear structures. A Frangi filter is similar to the Steger filter used in Zhou et al. (FIGS. 3A-3B)

Grid sampling: Sampling on a regular grid of size of g (Grid-g) placed on a lesion. When g is small, this is also called dense sampling.

Radial sampling: Sampling using polar coordinates on axes placed on the lesion with origin at the center of the lesion (Radial). The rationale behind this scheme is that a lesion generally follows a radially growing pattern (14).

Feature Pooling Schemes

The popular average pooling and spatial pooling schemes are investigated. Average pooling uses averaging of the class assignments across all patches. This is equivalent to building a normalized histogram, whereby each bin corresponds to a codeword in a codebook and the bin's value is proportional to the number of patches assigned to that codeword. Spatial pooling detects homogeneous regions inside a lesion and then uses average pooling in each homogeneous region. A lesion is segmented into 3 to 8 regions using the normalized cut method (FIG. 4). Tiny regions are grouped with nearby larger ones. Thus, after spatial pooling, a single vector (histogram) is produced for each segmented region. In the proposed method, a whole lesion is represented as a fully connected weighted graph, whose nodes correspond to homogeneous regions. The weight of an edge is the Euclidean distance between the vectors of the two connected nodes (regions). Then a lesion is represented using six features implemented in the graph measure toolbox (15), namely clustering coefficient, maximized modularity, characteristic path length, eccentricity for each vertex, radius, and diameter of the graph (graph eccentricity, radius, and diameter are not the same lesion measures defined in (2)). Tree and graph schemes have been proposed before (16-17), however, not for malignant classification. This proposed weighted graph model extends recent work in which a non-weighted graph lesion representation was employed for melanoma detection (18).

Codebook and Classifier Implementation Details

Codebooks are built using K-mean clustering on a set of patches obtained by randomly sampling 1,000 patches from every lesion so that every lesion contributes equally to the codebook construction. Thus, the evaluation uses transductive inference (19), i.e., in this classifier learning method labeled training data and unlabeled testing data were employed, while for testing labels were predicted for the latter. The number of cluster is 200 for wavelet features and 100 for color features. The overall performance is not sensitive to these choices. Separate codebooks are built for wavelet and color, and different codebooks for the three patch sizes: 16, 24, and 32. By default, average pooling is used, if not specified otherwise. This classifier uses support vector machines (SVMs) with a $\chi^2$ kernel, which is the state-of-the-art setting for BoF model. For graph theory features, a Gaussian kernel which is the common choice for SVMs is used. The threshold for the classifier's output was chosen by maximizing the average of sensitivity and specificity on the labeled training data. For classifier combination, simple ensemble averaging is used (weighted combination (20) yielded very similar results on this dataset).

The Effect of Number of Patches Sampled

Figure 5B:
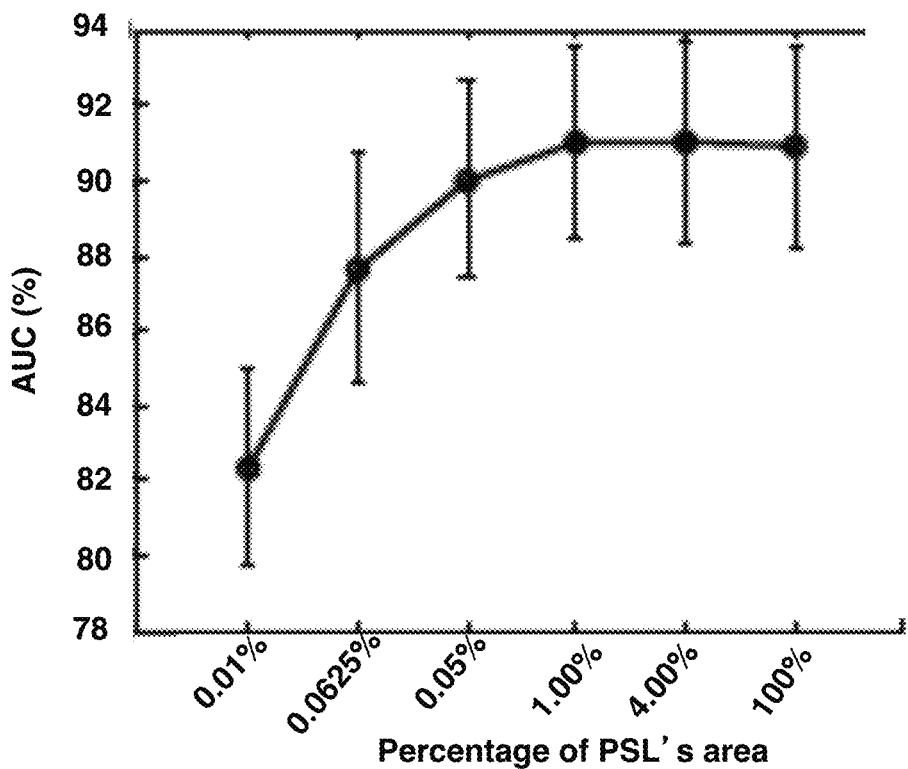

Choosing the same number of patches for all lesions is not reasonable, since lesions differ in size. Instead, a number of patches proportional to that lesion's area were chosen. Simple grid sampling was used and grid size was chosen from the set {1, 5, 10, 20, 40, 100}. Using a grid size g is equivalent to sampling approximately $(100/g^2)\%$ points from a lesion. A square patch of 24 pixels in size is used. FIGS. 5A-5B show that this percentage value affects significantly both performance measures. BAC starts to converge when the number of points approaches 4% of the lesion's area, while AUC converges earlier at about 1%. Thus, only 4% of points, i.e., Grid-5, from a lesion need to be sampled without decreasing performance significantly for both BAC and AUC.

The Effect of Sampling Strategy

Figure 6A:
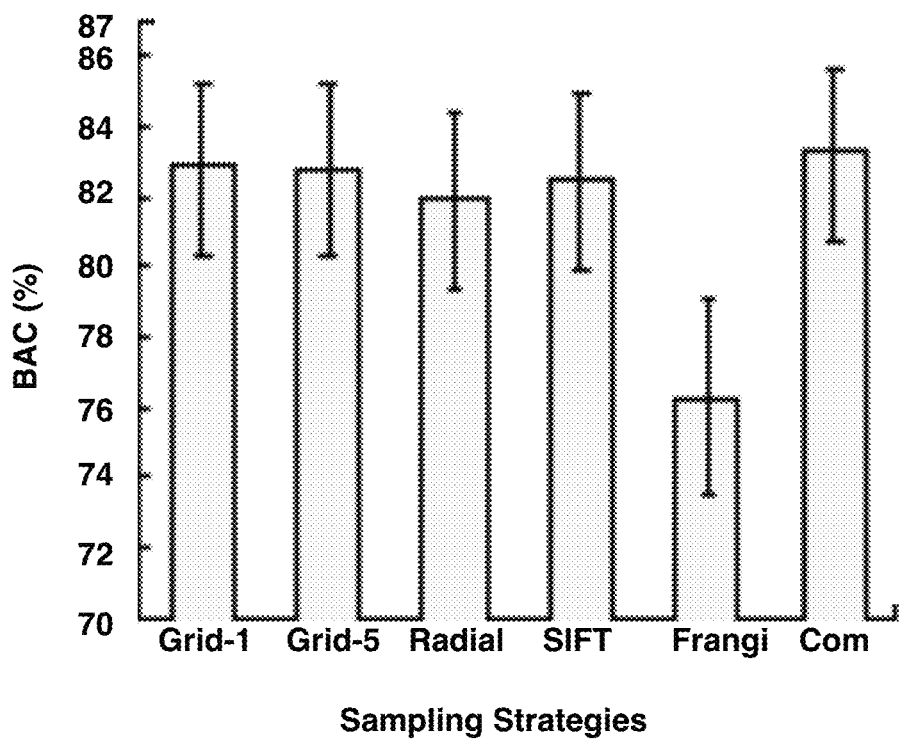
FIGS. 6A-6B are comparisons of various sampling schemes for 24×24 patches for balanced accuracy (BAC) (FIG. 6A) and area under the receiver operating characteristic curve (AUC) (FIG. 6B).
Figure 6B:
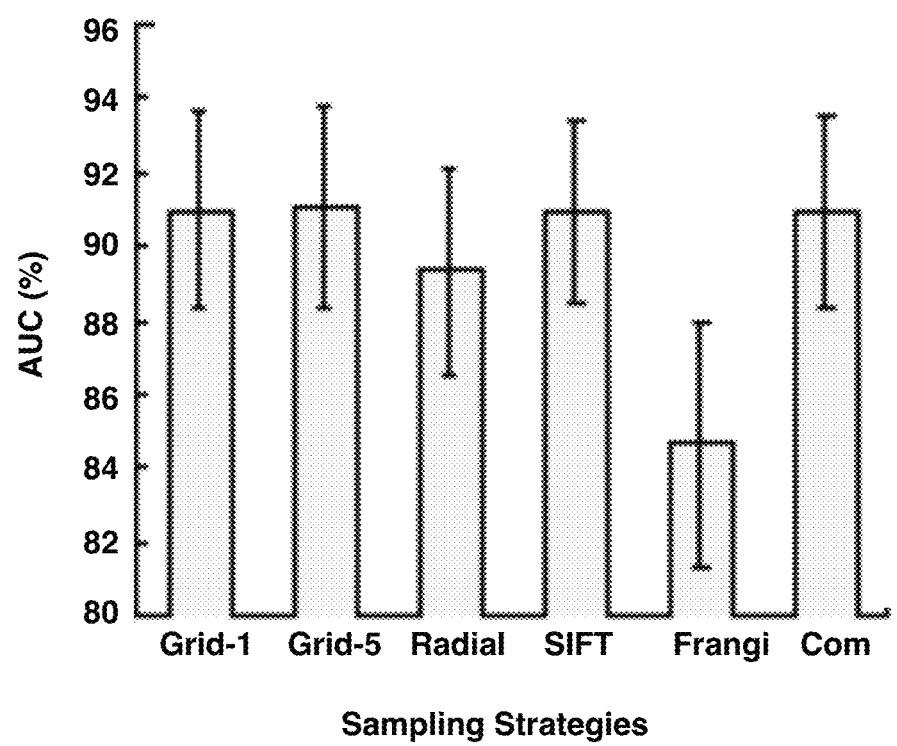

Now four lesion sampling methods, Grid-5, Radial, SIFT, and Frangi, are considered and the parameters and thresholds of the latter three methods are adjusted to retain 4% of all possible samples. In addition, the classifiers from Radial, SIFT, and Frangi are combined with Grid-1 (denoted as Com) to test whether classification accuracy improves when combining classifier training with interest points located at dermoscopic structures instead of simply using all possible points alone, i.e., Grid-1. FIGS. 6A-6B show that regular grid sampling Grid-5 provides results comparable to Radial, SIFT, and Frangi. A comparison between Com and Grid-1 reveals only a marginal improvement in BAC, but no improvement in AUC, when incorporating the more complicated interest point detectors instead of using simple dense sampling alone.

The Effect of Sampling at Multiple Scales

Figure 7A:
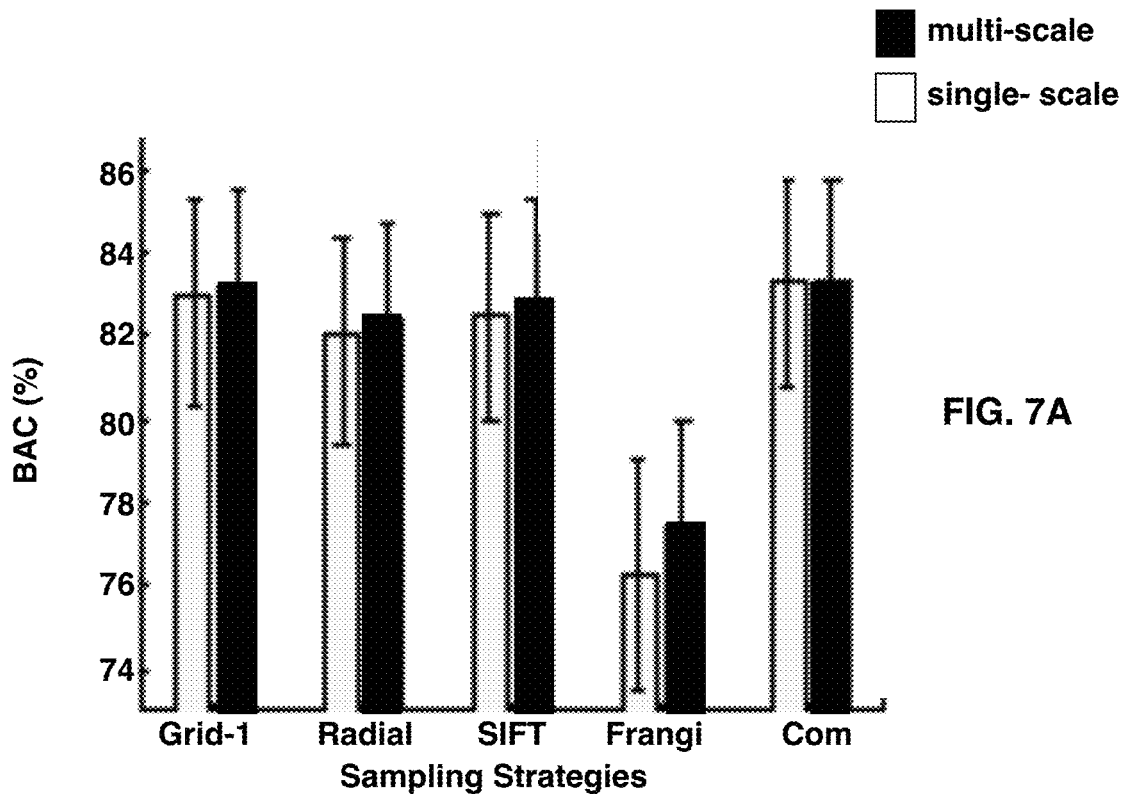
FIGS. 7A-7B are comparisons of single scale and multi-scale samplings for various sampling schemes for balanced accuracy (BAC) (FIG. 7A) and area under the receiver operating characteristic curve (AUC) (FIG. 7B).
Figure 7B:
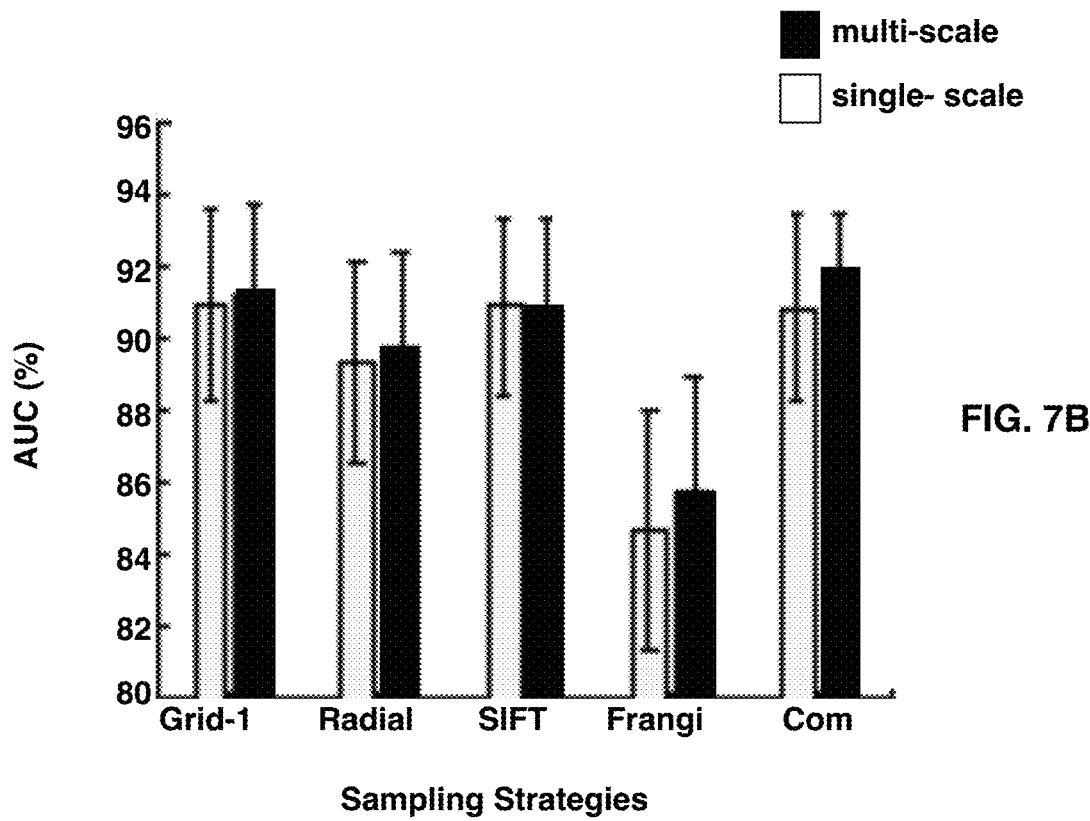

For each sampling strategy, square patches of size 16, 24, and 32 pixels are extracted, and the classifiers obtained from these three scales are grouped. For the multi-scale model of Com, 12 classifiers are ensembled from four sampling methods and three scales. FIGS. 7A-7B shows that multi-scale sampling can improve the performance of some methods compared to sampling at a single scale with patches of size 24. However, none of the multi-scale models in FIGS. 8A-8B is significantly better than Grid-1 using a single scale sampling.

The Effect of Spatial Pooling

Spatial pooling for patches of size 16×16 centered on every pixel are used, since it was observed empirically that a patch of size 16 performs better than size 24 or size 32 for graph theory features. The classifiers built from spatial pooling and Grid-1 are ensembled, and the combined model is denoted as DenSpa. DenSpa is compared with Grid-1, Com, and the multiscale models of Grid-1 and Com, denoted as GridMul and ComMul, respectively, in Table 3. DenSpa performs the best among the five schemes in all measures. The mean sensitivity of the other four methods without spatial pooling is below the 95% CI of DenSpa. The improvement for specificity is not so significant, but the AUC of DenSpa is significantly different from the other four methods as revealed by an unpaired t-test at 95% confidence level.

TABLE 3

Classification Performance

| Methods | Sensitivity (95% CI) | Fuzzy c-Means | AUC (std) |
| --- | --- | --- | --- |
| Grid-1 | 82.49 [79.16, 85.40] | 83.32 [81.39, 85.07] | 90.93 ± 2.67 |
| GridMul | 82.31 [78.92, 85.18] | 84.15 [82.28, 85.88] | 91.16 ± 2.55 |
| Com | 81.96 [78.67, 84.97] | 84.68 [82.82, 86.37] | 90.87 ± 2.60 |
| ComMul | 82.40 [79.16, 85.40] | 84.19 [82.37, 85.97] | 90.99 ± 2.53 |
| DenSpa | 86.17 [83.11, 88.80] | 84.68 [82.82, 86.37] | 92.71 ± 2.25 |

EXAMPLE 4

Portable Library for Melanoma Detection: Comparison of Smartphone Implementation with Desktop Application The automated procedure for lesion classification is based on the bag-of-features framework (3,9) and comprises the main steps of lesion segmentation, feature extraction, and classification.

Dataset

A total of 1300 artifact free images are selected: 388 were classified by histological examination as melanoma and the remaining 912 were classified as benign.

Image Segmentation

In addition to the lesion, images typically include relatively large areas of healthy skin, so it is important to segment the image and extract the lesion to be considered for subsequent analysis. To reduce noise and suppress physical characteristics, such as hair in and around the lesion that affect segmentation adversely, a fast two-dimensional median filtering (21) is applied to the grey scale image. The image is then segmented using three different segmentation algorithms, namely ISODATA (iterative self-organizing data analysis technique algorithm) (22), fuzzy c-means (23-24), and active contour without edges (25). The resulting binary image is further processed using morphological operations, such as opening, closing, and connected component labeling (26). When more than one contiguous region is found, additional processing removes all regions except for the largest one. The end result is a binary mask that is used to separate the lesion from the background.

Feature Extraction

Among the criteria employed by dermatologists to detect melanoma, as described by Menzies rules (27) and the 7-point list (28), texture analysis is of primary importance, since, among other things, malignant lesions exhibit substantially different texture patterns from benign lesions. Elbaum et al. (29) used wavelet coefficients as texture descriptors in their skin cancer screening system MelaFindR and other previous work (9) has demonstrated the effectiveness of wavelet coefficients for melanoma detection. Therefore, this library includes a large module dedicated to texture analysis.

Feature extraction works as follows: for a given image, the binary mask created during segmentation is used to restrict feature extraction to the lesion area only. After placing an orthogonal grid on the lesion, patches of size K×K pixels were sampled repeated from the lesion, where K is user defined. Large values of K lead to longer algorithm execution time, while very small values result in noisy features. Each extracted patch is decomposed using a 3-level Haar wavelet transform (30) to get 10 sub-band images. Texture features are extracted by computing statistical measures, like mean and standard deviation, on each sub-band image, which are then are put together to form a vector that describes each patch.

Image Classification

A support vector machine (SVM) is trained using a subset (training set) of the total images available, and the resulting classifier is used to determine whether the rest of the images, i.e., test set, are malignant or benign (3).

Training:

1. For each image in the training set, (a) Segment the input image to extract the lesion.

(b) Select a set of points on the lesion using a rectangular grid of size M pixels.

(c) Select patches of size K×K pixels centered on the selected points.

(d) Apply a 3-level Haar wavelet transform on the patches.

(e) For each sub-band image compute statistical measures, namely mean and standard deviation, to form a feature vector $F_i = \{m_1, sd_1, m_2, sd_2, \ldots\}$.

2. For all feature vectors $F_i$ extracted, normalize each dimension to zero mean and unit standard deviation.

3. Apply the K-means clustering (31) to all feature vectors $F_i$ from all training images to obtain L clusters with centers $C = \{C_1, C_2, \ldots, C_L\}$.

4. For each training image build a L-bin histogram. For feature vector $F_i$, increment the jth bin of the histogram such that $\min_j C_i - F_i$.

5. Use the histograms obtained from all the training images as the input to a SVM classifier to obtain a maximum margin hyperplane that separates the histograms of benign and malignant lesions.

Figure 8:
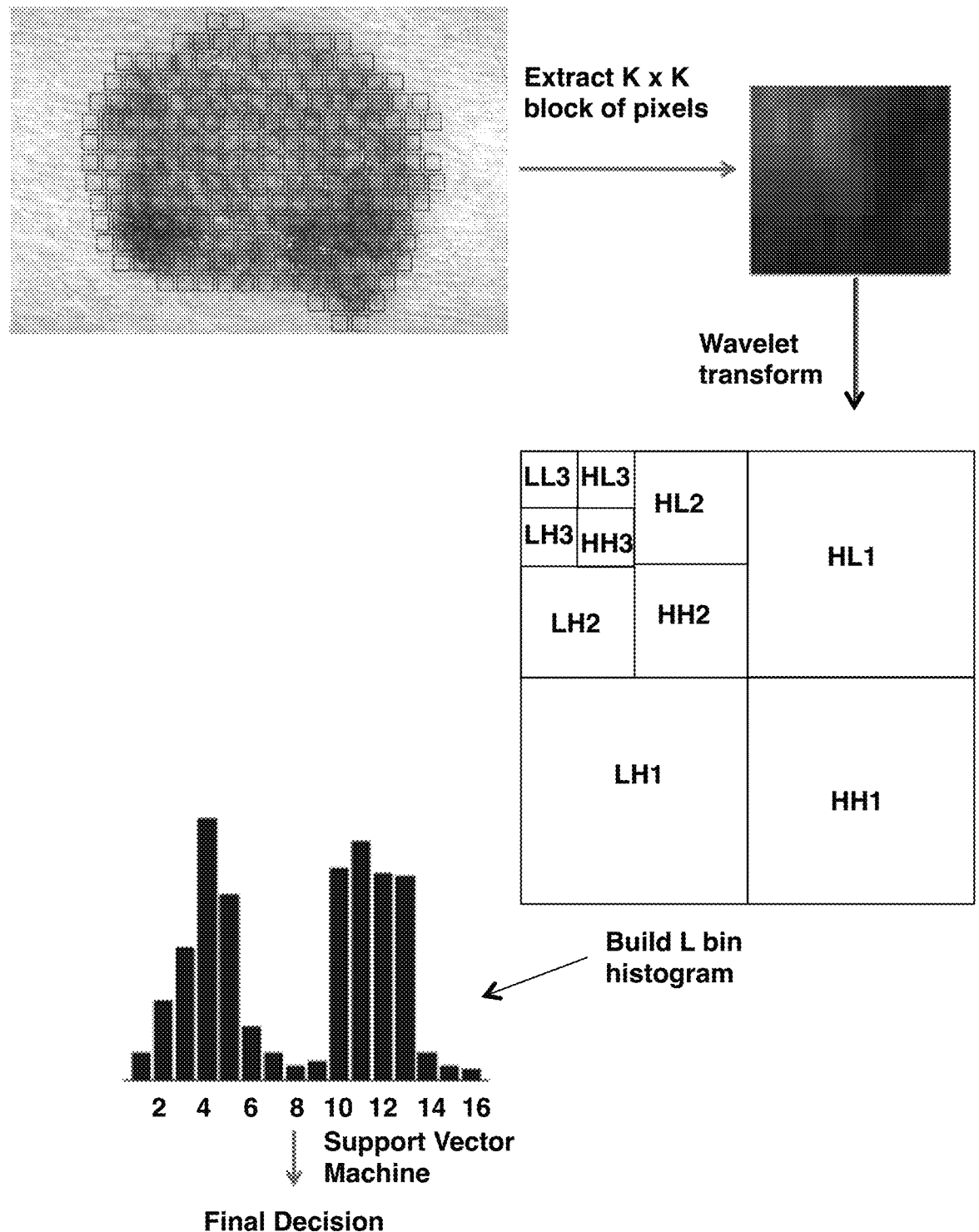
FIG. 8 depicts the lesion classification process with steps selecting a patch from the lesion, applying a 3-level Haar wavelet transform, extracting texture features, building a histogram using the cluster centers obtained during training, and inputting the histogram to the trained SVM classifier to classify the lesion.
Figure 9A:
FIGS. 9A-9D depicts the scanning application on an Apple® iPhone® device.
Figure 9B:
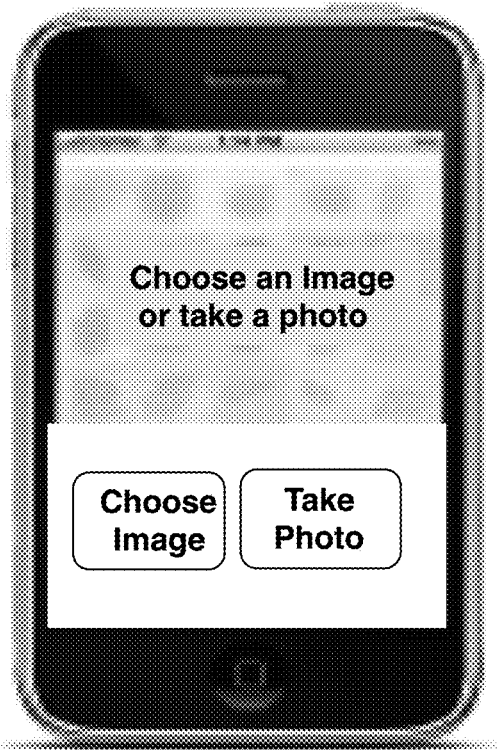
Figure 9C:
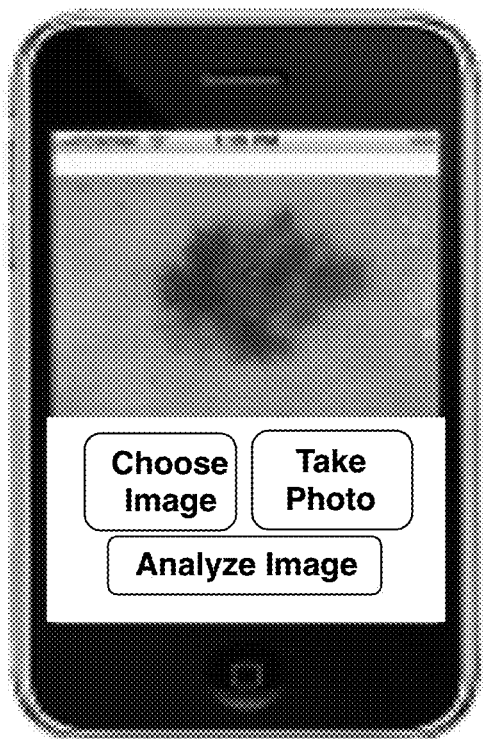
Figure 9D:
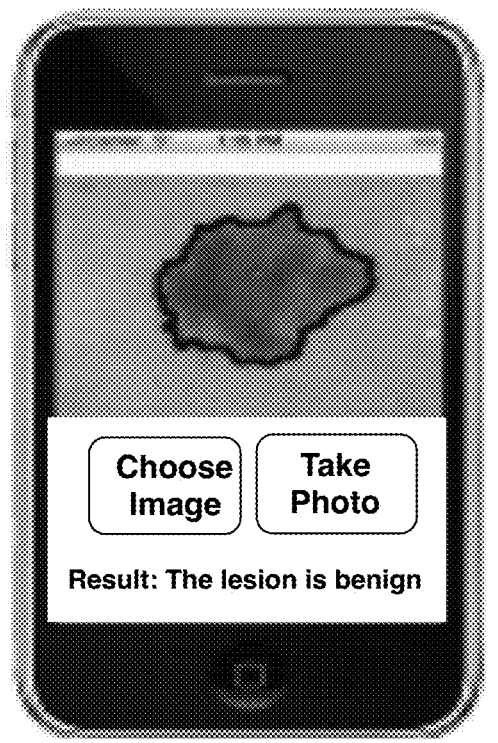

The value of parameter M is a trade-off between accuracy and computation speed. Small values of M lead to more accurate classification results, but computation time increases accordingly. When the algorithm runs on the smartphone device, to reduce computation time, M=10 was chosen for grid size, K=24 for patch size, and L=200 as the number of clusters in the feature space. By exhaustive parameter exploration (9), it was determined that these parameters are reasonable settings for the dataset. FIG. 8 summarizes in graphical form the feature extraction and classification steps of the proposed procedure.

Testing: Each test image is classified using the following steps:

1. Read the test image and perform Steps 1(a)-(e) and 2 in the training algorithm, to obtain a feature vector $F_i$ that describes the lesion.

2. Build an L-bin histogram for the test image. For all feature vectors $F_i$ extracted from the image, increment the jth bin of the histogram, such that $\min j\, C_i - F_1$, where this time the cluster centers $C_i$ are the centers identified in Step 3 of the training procedure.

3. Submit the resulting histogram to the trained SVM classifier to classify the lesion.

For test images, likelihood of malignancy can be computed using the distance from the SVM hyperplane. Training of the SVM classifier was performed off-line on a desktop computer, while testing is performed entirely on the smartphone device.

iPhone 4® Implementation

A menu based application is developed that implements the automated procedure outlined in the previous sections (FIGS. 9A-9D). The user can take a picture of a lesion or load an existing image from the phone photo library. The image is then analyzed on the phone in quasi real time and the results of classification are displayed on the screen.

Comparison of the Segmentation Methods

To assess the performance of the proposed application the automatic segmentation is compared with manual segmentation. For each image an error, defined (32) as the ratio of the nonoverlapping area between automatic and manual segmentation divided by the sum of the automatic and manually segmented images, was calculated. The error ratio is zero when the results from automatic and manual segmentation match exactly, and 100 percent when the two segmentations do not overlap. Thus the error is always between zero and 100 percent, regardless of the size of the lesion. An earlier study found that when the same set of images was manually segmented by more than one expert, the average variability was about 8.5 percent (32). This same figure was used and included an additional tolerance of 10 percent error to account for the large number of images in the dataset. Therefore, the cutoff for error ratio was set to 18.5 percent, considering that a lesion is correctly segmented by the automated procedure if the error ratio is less than 18.5 percent.

Figure 10A:
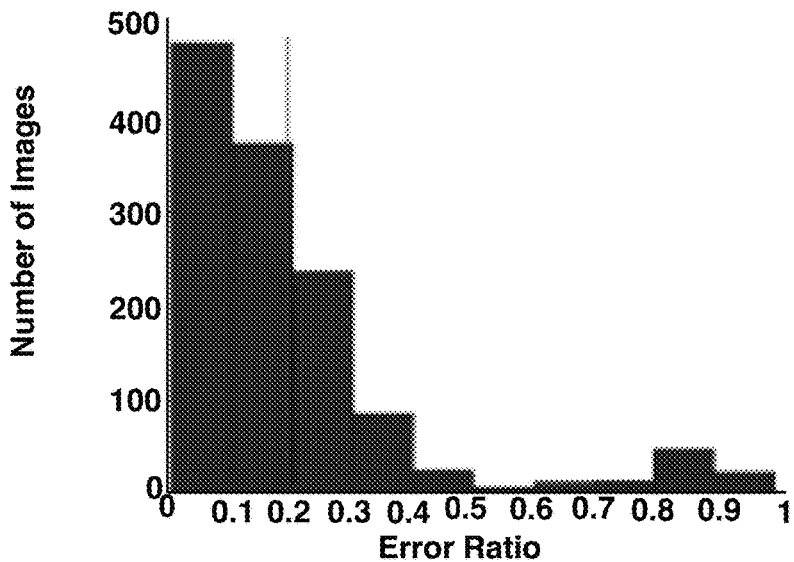
FIGS. 10A-10C illustrate the error ratio distribution of segmentation methods Fuzzy-C Means (FIG. 10A), ISO-DATA (FIG. 10B) and Active Contour (FIG. 10C) on the dataset of 1300 skin lesion images. The dotted line marks the threshold for correct segmentation.
Figure 10B:
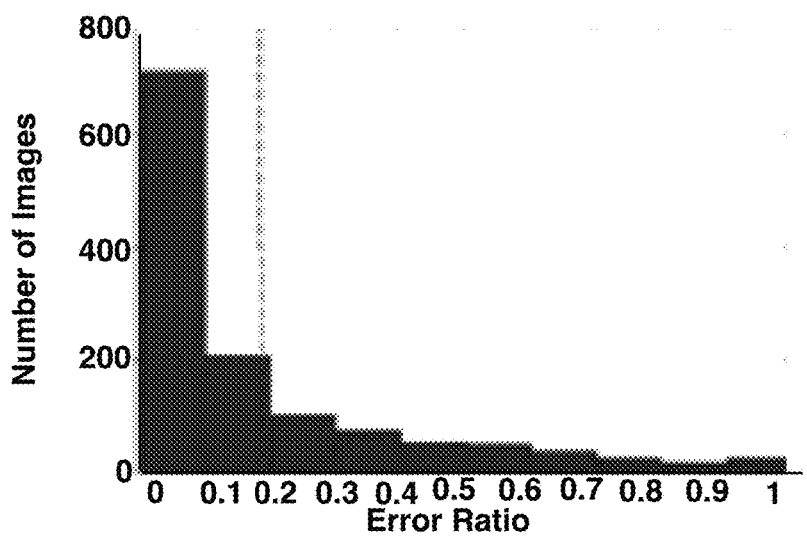
Figure 10C:
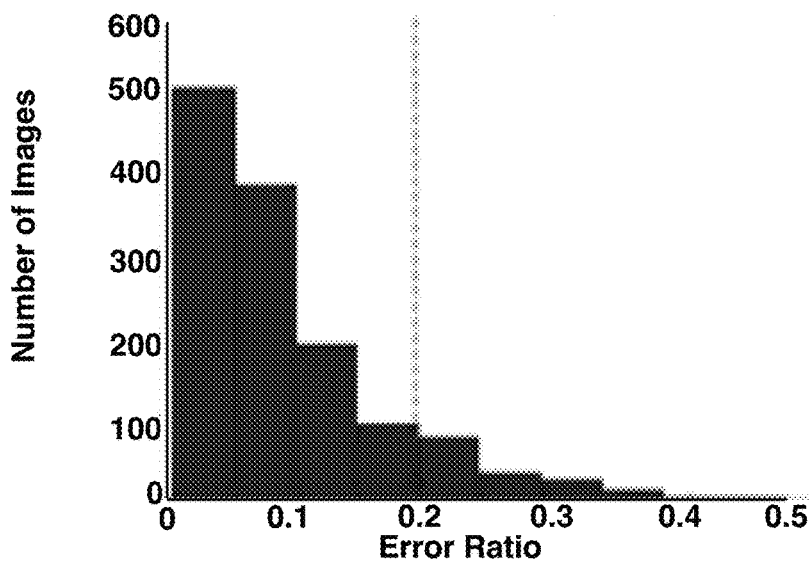

The dataset of 1300 skin lesion images was segmented using the three segmentation techniques mentioned previously. Table 4 shows the number of images correctly segmented, and the mean and standard deviation of error for all images. The active contour method was found to be the most accurate, as it had the highest number of images segmented correctly and least mean error ratio. ISODATA and Fuzzy c-Means, in that order, followed the active contour method in accuracy. FIGS. 10A-10C show the error distribution of three segmentation methods, where the number of images is plotted against the error ratio. The threshold of 18.5% is marked as the vertical dotted line. Of the 1300 images examined, 754 images had error ratio below 8.5% (variability of error among domain experts), 1147 images had error ratio below 18.5% (threshold for correct segmentation), and 153 images with error ratio above 18.5%. This seemingly high error is due to the fact that manual lesion segmentation yields a smooth boundary, while automatic segmentation detects fine edges on the border.

TABLE 4

Performance of Segmentation Techniques

|  | ISODATA | Fuzzy c-Means | Active Contour |
|---|---|---|---|
| Images correctly segmented | 883 | 777 | 1147 |
| Images incorrectly segmented | 417 | 523 | 153 |
| Mean Error | 19.46% | 20.40% | 9.69% |
| Standard Deviation Error | 22.41 | 19.80 | 6.99 |

Classification Accuracy 10 trials of 10-fold cross validation were performed on the set of 1300 images. The dataset was divided into 10 folds, nine folds with 39 melanoma and 92 benign lesions and the remaining fold with 37 melanoma and 87 benign lesions. Of the 10 folds, nine were used for training and one was used for testing. 10 rounds of validation were performed where each fold was chosen for testing, to get 10×10=100 experiments. An average over these 100 experiments demonstrated 80.76% sensitivity and 85.57% specificity.

Figure 11:
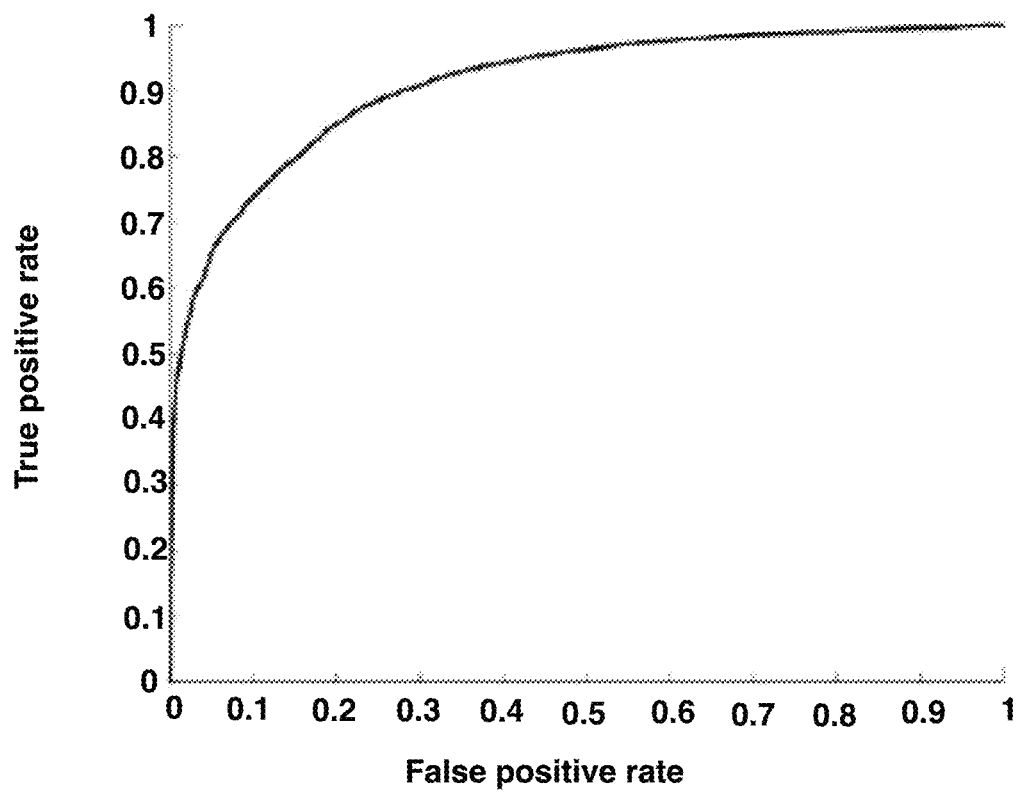
FIG. 11 depicts the ROC curve for lesion classification.

FIG. 11 shows the receiver operating characteristic (ROC) curve of classification computed from testing data (33), whereby the area under the curve is 91.1%. The threshold to maximize the mean of sensitivity and specificity on the training set was chosen. The 95% confidence interval on testing data was estimated using a binomial distribution for sensitivity to be [77.1%, 83.9%] and for specificity was estimated to be [83.5%, 87.4%]. The classification accuracy is same on the desktop computer and iPhone 4® smartphone.

Execution Time

The time taken for active contour segmentation and classification on the Apple® iPhone 4® smartphone is compared with a typical desktop personal computer (2.26 GHz Intel® Core™ 2 Duo with 2 GB RAM). The classification time includes time taken for feature extraction. The average image size in the dataset is 552×825 pixels. Table 5 shows computation time in seconds for both platforms. For the largest image in the dataset which has dimensions 1879×1261 pixels, segmentation takes 9.71 sec and classification takes 2.57 sec on the iPhone®. Thus, the whole analysis procedure takes under 15 sec to complete. This proves that the library is light enough to run on a smartphone which has limited computation power.

TABLE 5

| | Computation Time | |
|---|---|---|
| Mean time (sec) | Apple ® iPhone 4 ® | Desktop computer |
| Segmentation | 883 | 777 |
| Classification | 417 | 523 |

EXAMPLE 5

Detection of Blue-whitish Veil in Melanoma Using Color Descriptors

Dataset

There were 1,009 ELM skin lesion images collected from a widely available commercial database (7), with full annotations for the ABCD rule and 7-point checklist. In this dataset, 252 images are benign, 757 images are melanoma. Presence of 163 blue-whitish veil skin lesions in this dataset were labeled by expert dermatologists.

Local Classification

For each local neighborhood of pixels, color histograms were computed, i.e. distribution of pixel intensities in various color models (RGB, HSV, YUV, O1O2O3, Nrgb). These color models are used because of their invariance to change in lighting conditions (34). These local features are used for detection of color in that local neighborhood.

Training: For all images belonging to the training set perform the following steps:

1) Segment the input image to extract the skin lesion (ROI).

2) Perform transformation of the input RGB image to different color spaces ($O_1O_2O_3$, HSV, Nrgb, YUV).

3) From ROI select non-overlapping patches of size K×K pixels.

4) Extract low-level color features from these K×K patches. For each channel in all color spaces build a separate P bin histogram $H_i$.

a) For all pixels belonging to the extracted patch, increment the $j^{th}$ bin of histogram where $j=I_c/P \times M_c$. $I_c$ is pixel intensity and $M_c$ is maximum intensity in the specified color space.

b) Concatenate all the extracted histograms to form a feature vector $F_i=\{H_1, H_2, \ldots\}$, for a given patch in the image.

c) Based on prior knowledge of the patch color, mark the feature vector as blue-whitish veil or not blue-whitish veil.

5) Perform step 4 for all the patches in the ROI to obtain $F_i$'s.

6) Input all $F_i$ extracted from step 5 to linear SVM to obtain maximum margin hyperplane.

Testing: For all images belonging to the testing set perform the following steps:

1) Perform steps 1-4 from training.

2) For each feature vector $F_i$ belonging to a patch. in the image use SVM to classify as blue-whitish veil or not blue-whitish veil.

3) Classify all extracted patches in the ROI.

Global-level Classification: Approach 1

In the second step local classification features are used to perform a global-level classification. Experiments were performed with two choices of global level classifiers. The first global classifier builds a probability distribution of the local classification result. The second global classifier uses a trivial approach to mark positive presence of color, when one or more local neighborhoods have been marked with presence of color. Training: After applying patch level classification on all images in the training set, the following steps were performed:

1) For each patch in the training image perform patch-level classification to obtain probability estimate of the membership of the patch to blue-whitish veil/not blue-whitish veil.

2) Build a B bin, global-level histogram $G_i$ for each training image. For all patches in the training image:

a) Increment the $j^{th}$ bin of the histogram $G_i$, where $j$=round($P_{es}$/B), $P_{es}$ is the probability estimate of a patch membership to blue-whitish veil/not blue-whitish veil.

3) Perform steps 1 and 2 for all images in the training set to obtain histogram $G_i$.

4) Input all $G_i$ obtained from step 3 to linear SVM to obtain maximum margin hyperplane.

Testing:

1) Perform steps 1 and 2 for a test image to obtain histogram $G_i$.

2) Use SVM from the training to mark presence of blue-whitish veil in the given test image.

Global-level Classification: Approach 2

In this classifier a trivial approach is used, i.e., an image with one or more blue-whitish patch is marked for positive presence of blue-whitish veil. If none of the patches in the image have blue-whitish veil, then blue-whitish veil is absent from the image.

Classification Results

A set of 326 non blue-whitish veil lesions were selected randomly and were combined with 163 blue-whitish veil lesion to form a subset. The reason for subset selection is to have a proportionate representation of the both classes. For each trial of cross-validation a new subset of non blue-whitish veil images was selected randomly from the whole dataset.

Figure 12:
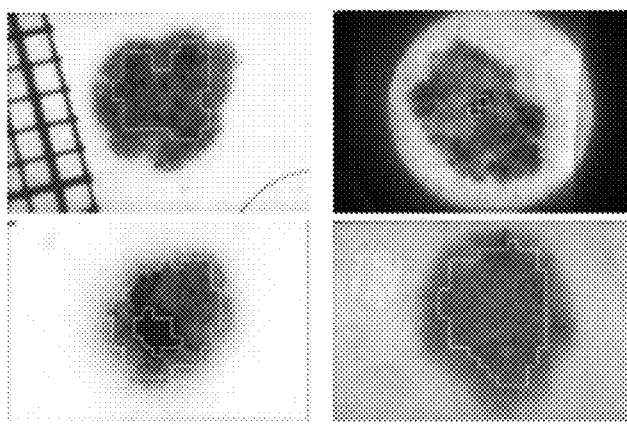
FIG. 12 depicts the results of blue-whitish veil detection on skin lesion images.

Ten trials of 10-fold cross validation were performed on a set of 489 images. The dataset was divided into 10 folds, nine folds with 16 blue-whitish veil lesions and 32 lesions where it is absent and the remaining fold with 19 blue-whitish veil lesions and 38 non blue-whitish veil lesions. Out of the 10 folds, nine are used for training and one for testing. 10 rounds of validation were performed, such that each fold was chosen for testing at least once. Therefore there were 10×10=100 experiments. An averaged over 100 experiments was obtained which demonstrated sensitivity and specificity of the algorithm. FIG. 12 depicts the results of blue-whitish veil detection on th skin lesion images. Table 6 shows the classification accuracy of both global level approaches. It was observed that the trivial approach performs better.

TABLE 6

Classification Accuracy of blue-whitish veil detection

|  | Sensitivity | Specificity |
| --- | --- | --- |
| Global-level Approach 1 | 90.59% | 65.50% |
| Global-level Approach 2 | 95.27% | 63.90% |

The low specificity of the blue-whitish veil detection is because of large false positives due to regression structures. Regression structures are one of the minor criterion of the 7-point checklist. It is defined as associated white and blue areas which are virtually indistinguishable from blue-whitish veil (7). Experiments also were performed for detection of both blue-whitish veil and regression structures. Table 7 shows the classification accuracy of both global level approaches. It was observed that the specificity has increased substantially because of lower false positives.

TABLE 7

Classification Accuracy of blue-whitish veil and regression structures

|  | Sensitivity | Specificity |
| --- | --- | --- |
| Global-level Approach 1 | 95.64% | 72.30% |
| Global-level Approach 2 | 96.66% | 68.28% |

Figure 13A:
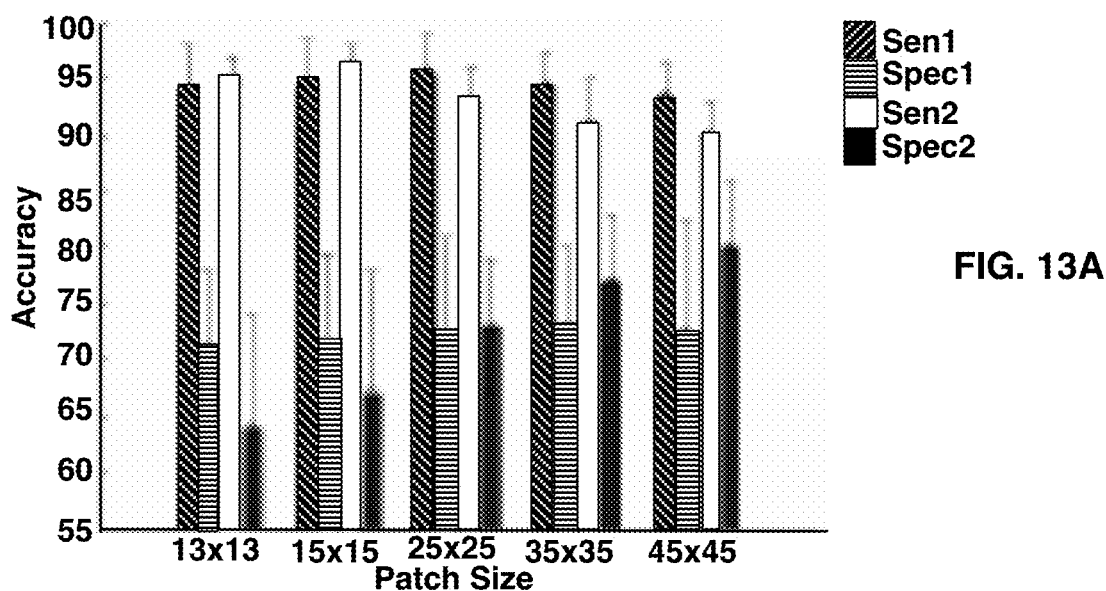
FIGS. 13A-13B depict varying patch size (FIG. 13A) and varying local bin size (FIG. 13B). Sen1 and Spec1 represent sensitivity and specificity of first global approach. Sen2 and Spec2 represent sensitivity and specificity of second global approach.

Parameter exploration was performed to find the most suitable choice of the non-overlapping square patch size used for extraction of local color features. FIG. 13A shows classification accuracy by varying the patch size. It was observed that small patch size introduce noise and for large patch sizes the performance degrades because good discriminative local features can no longer be detected. It also was observed that first global approach is more stable to the choice of patch size.

Figure 13B:
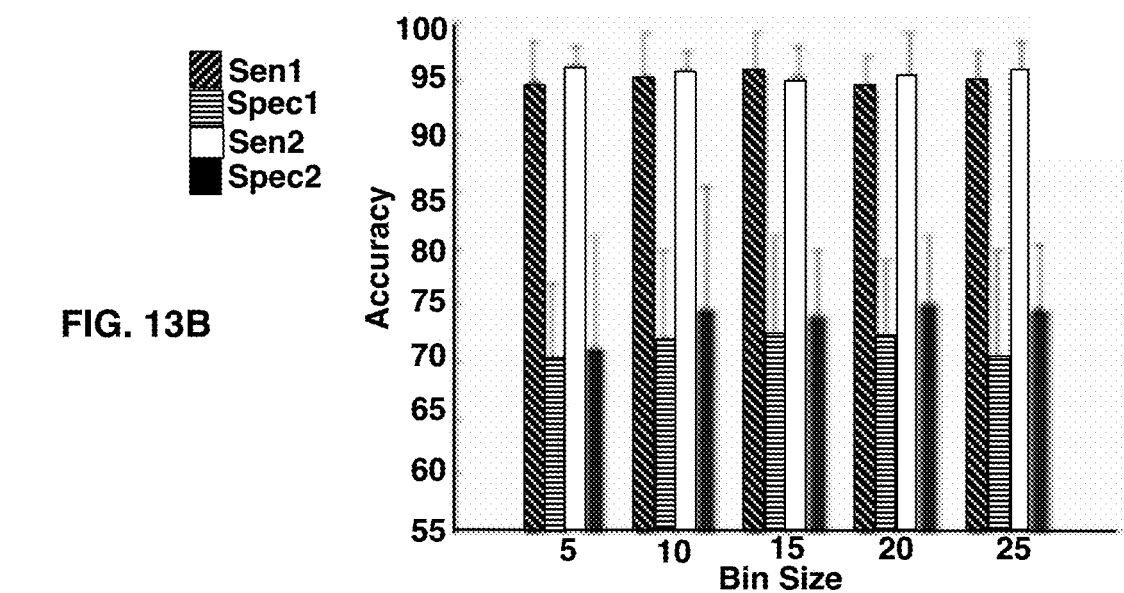
Figure 14:
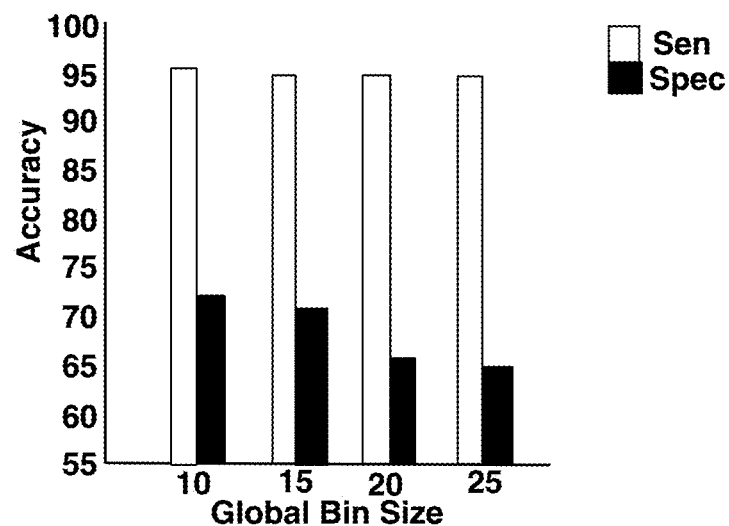
FIG. 14 depicts varying global bin size. Blue bar represents sensitivity and red bar represents specificity.

Parameter exploration was performed to find the most suitable choice for histogram quantization of color models to represent local features. FIG. 13B shows the classification accuracy with varying bin size of local level color histograms. The first global approach depends upon the quantization of the global-level feature histogram. FIG. 14 illustrates that smaller bin size of histogram has better specificity.

Simulation of Variance in Lighting Condition

Figure 15A:
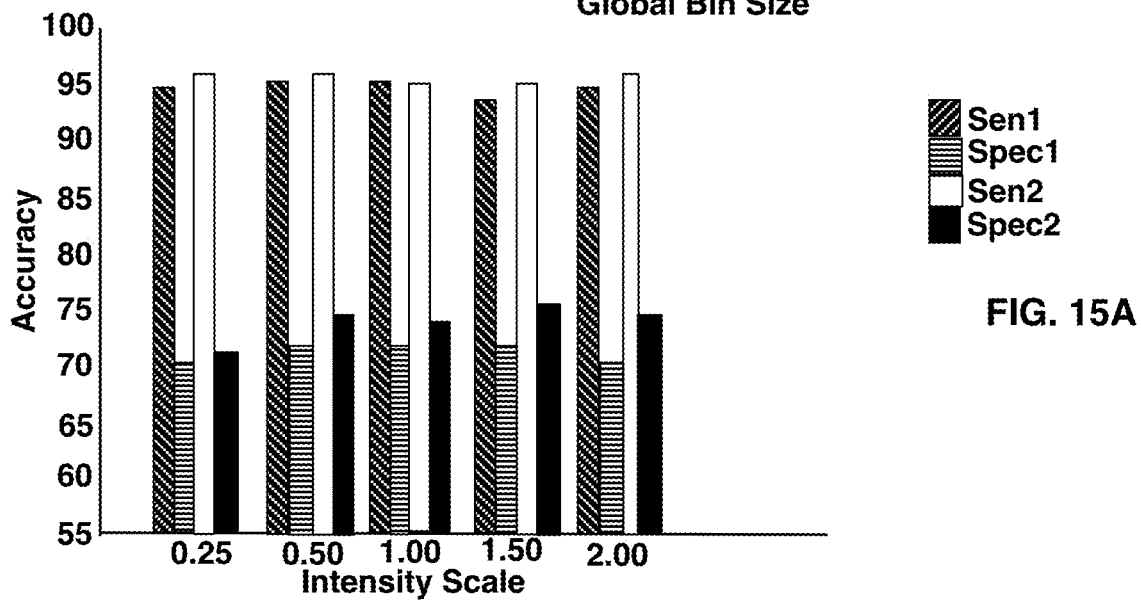
FIGS. 15A-15B depict scaling light intensity (FIG. 15A) and shifting light intensity (FIG. 15B). Sen1 and Spec1 represent sensitivity and specificity of first global approach. Sen2 and Spec2 represent sensitivity and specificity of second global approach.
Figure 15B:
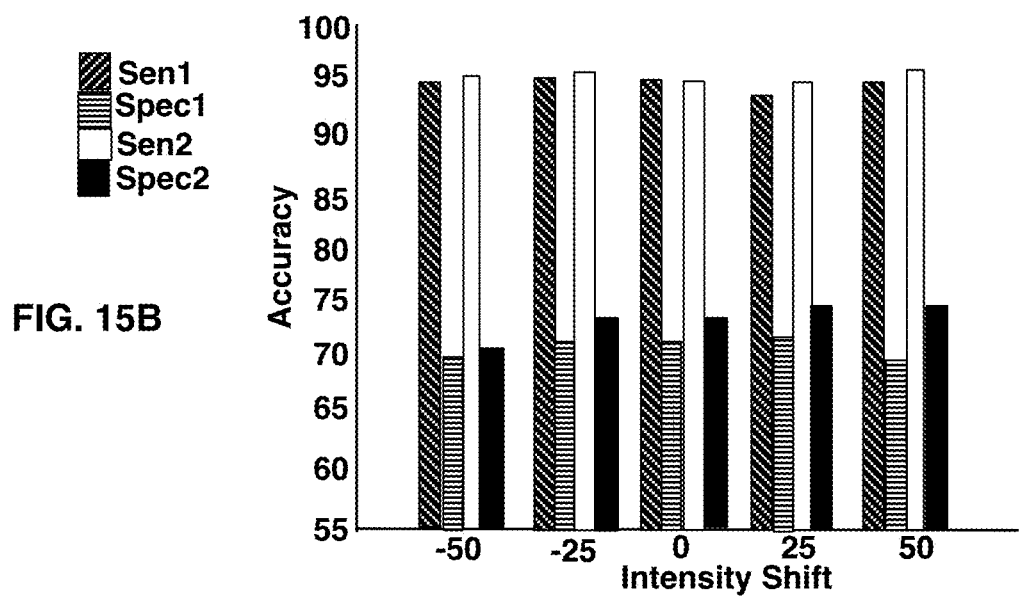

Variance in lighting conditions was simulated by scaling and shifting the pixels intensity values in the dataset to show stability of the algorithm. The pixels intensity was multiplied by a scaling factor that varies from 0.25 to 2.0. FIG. 15A shows that the classification accuracy is invariant to light intensity scaling. Illumination change also was simulated by shifting pixels intensity values in the dataset images. The pixels intensity was shifted by adding and subtracting a value that varies from −50 to 50. FIG. 15B shows that the classification accuracy is invariant to light intensity shifting.

EXAMPLE 6

Instantiation of 7-point Checklist on Smart Handheld Devices

Dataset

Only images considered as low difficulty by the experts (7) were chosen. There were 385 low difficulty images in the database (7) and the segmentation methods described herein could provide a satisfactory boundary for 347 (90.13%) of them. In the selected set of 347 images: 110 were classified by the 7-point list as melanoma and the remaining 237 were classified as benign.

Feature Extraction

To identify a region of interest (ROI), an image is first converted to greyscale, and then fast median filtering (21) for noise removal is performed, and followed by ISODATA segmentation (23), and several morphological operations. From the ROI, color and texture features relating to each criterion on the 7-point checklist were extracted, as follows.

I. Texture Features: They provide information on the various structural patterns (7) of 7-point checklist, such as pigmentation networks, vascular structures, and dots and globules present in a skin lesion. Haar wavelet coefficients (9) and local binary patterns (34) can be utilized for melanoma detection.

Haar Wavelet: From the ROI non-overlapping K×K blocks of pixels were selected, where K is a user defined variable. Computation time for feature extraction is directly proportional to the block size K. The block of pixels is decomposed using a three-level Haar wavelet transform (30) to get 10 sub-band images. Texture features were extracted by computing statistical measures, like the mean and standard deviation, on each sub-band image, which are then combined to form a vector $W_i=\{m_1, sd_1, m_2, sd_2, \ldots\}$. Haar wavelet extraction for texture feature is as follows:

1) convert the color image to greyscale; select a set of points in the ROI using a rectangular grid of size M pixels.
2) Select patches of size K×K pixels centered on the selected points.
3) Apply a 3-level Haar wavelet transform on the patches.
4) For each sub-band image compute statistical measures, namely mean and standard deviation, to form a feature vector $W_i=\{m_1, sd_1, m_2, sd_2, \ldots\}$.
5) For all feature vectors $W_i$ extracted, normalize each dimension to zero-mean and unit-variance.
6) Apply K-means clustering (31) to all feature vectors $W_i$ from all training images to obtain L clusters with centers $C=\{C_1, C_2, \ldots, CL\}$.
7) For each image build an L-bin histogram $H_i$. For feature vector $W_i$, increment the jth bin of the histogram such that $\min_j \|C_j - W_i\|$.

The value of parameter M is a trade-off between accuracy and computation speed. When the algorithm runs on a handheld device to reduce computation time, M=10 for the grid size, K=24 for patch size, and L=200 as the number of clusters in the feature space were chosen. As previously demonstrated, these parameters are reasonable settings (9).

Local Binary Pattern (LBP): LBP is a robust texture operator (35) defined on a greyscale input image. It is invariant to monotonic transformation of intensity and invariant to rotation. It is derived using a circularly symmetric neighbor set of P members on a circle of radius R denoted by $LBP_{PR}^{riu}$ (35). The parameter P represents the quantization of angular space in the circular neighborhood, and R represents the spatial resolution. A limited number of transitions or discontinuities (0/1 changes in LBP) are allowed to reduce the noise and for better discrimination of features. The number of transitions in LBP were restricted to P, and transitions greater than that are considered equal. An occurrence histogram of LBP with useful statistical and structural information is computed as follows:

1) Convert the color image to greyscale.
2) Select pixels belonging to ROI and compute local binary pattern $LBP_{PR}^{riu}$ (35).
3) Build an occurrence histogram, where the $j^{th}$ bin of the histogram is incremented, if the number of transitions in LBP is j.
4) Repeat steps 2 and 3 for all pixels in ROI.

The occurrence histograms for $LBP_{16,2}$ and $LBP_{24,3}$ were built and concatenate them to form a feature vector $L_i$.

II. Color Features: Detection of the 7-point checklist criteria, such as blue-whitish veil and regression, which consist of mixtures of certain colors, can be achieved by analyzing the color intensity of pixels in the lesion (36). To reduce the variance due to the lighting conditions in which dermoscopic images were taken, the HSV and LAB color spaces were considered also, which are invariant to illumination changes (34).

Color Histograms: To extract the color information of a lesion, a color histogram was computed from the intensity values of pixels belonging to the ROI. Additional images in the HSV and LAB color spaces are obtained from the original RGB image. The intensity range of each channel is divided into P fixed-length intervals. For each channel a histogram was built to keep count of the number of pixels belonging to each interval, resulting in a total of nine histograms from three color spaces. Statistical features, such as standard deviation and entropy (Eq. 9), of the nine histograms are also extracted as features for classification. More specifically, entropy is defined as $$\text{entropy} = \sum_{i=1}^{P} f(histogram[i]) \quad \text{(Eq. 9)}$$

where histogram[i] is the normalized pixel count of $i^{th}$ bin and $$f(n) = \begin{cases} n \times \log 2(n) & \text{if } n > 0 \\ 0 & \text{if } n = 0 \end{cases}.$$

The color histogram feature extraction steps are as follows:
1) Obtain skin lesion image in HSV and LAB color space from input RGB image
2) For each channel in all three color spaces build a separate P bin histogram
3) For all pixels belonging to ROI, increment the $j^{th}$ bin of histogram where $j=I_c/P \times M_c$. $I_c$ and $M_c$ are pixel intensity and maximum intensity in the specified color space.
4) Compute the standard deviation and entropy of the histogram.
5) Repeat steps 3 and 4 for all the channels in RGB, HSV, and LAB color space. Color histogram and statistical features are combined to form a feature vector $C_i$.

Classification

The features from color histogram $C_i$, Haar wavelet $H_i$, and LBP $L_i$ are combined to form $F_i=\{C_i, H_i, L_i\}$. For each criterion in the 7-point checklist a filtered feature selection was performed to obtain a subset of $F_i$ with the highest classification accuracy. Correlation coefficient values (between $F_i$ and each criterion) are used as the ranking criterion in the filters. The size of the subset and the parameters of the linear support vector machine (SVM) are obtained by grid search. Each criterion requires both training and testing.

Training: The training algorithm is as follows:
1) Segment the input image to obtain region of interest.
2) Extract Color histogram, Haar wavelet, and Local binary pattern. Concatenate them to form feature vector $F_i$.
3) Repeat steps 1 and 2 for all training images.
4) Perform filter feature selection to choose a subset of features $S_i$ from $F_i$.
5) Input $S_i$ to linear SVM to obtain maximum margin hyperplane.

Testing: Image classification is performed as follows:
1) Read the input image and perform steps 1 and 2 from the training algorithm.
2) For each criterion use the SVM coefficients obtained from training to make a prediction.
3) Scores from all major and minor criteria are summed up. If the score is greater than or equal to 3 then lesion is classified as melanoma, otherwise as benign.

Classification Results

Figure 16A:
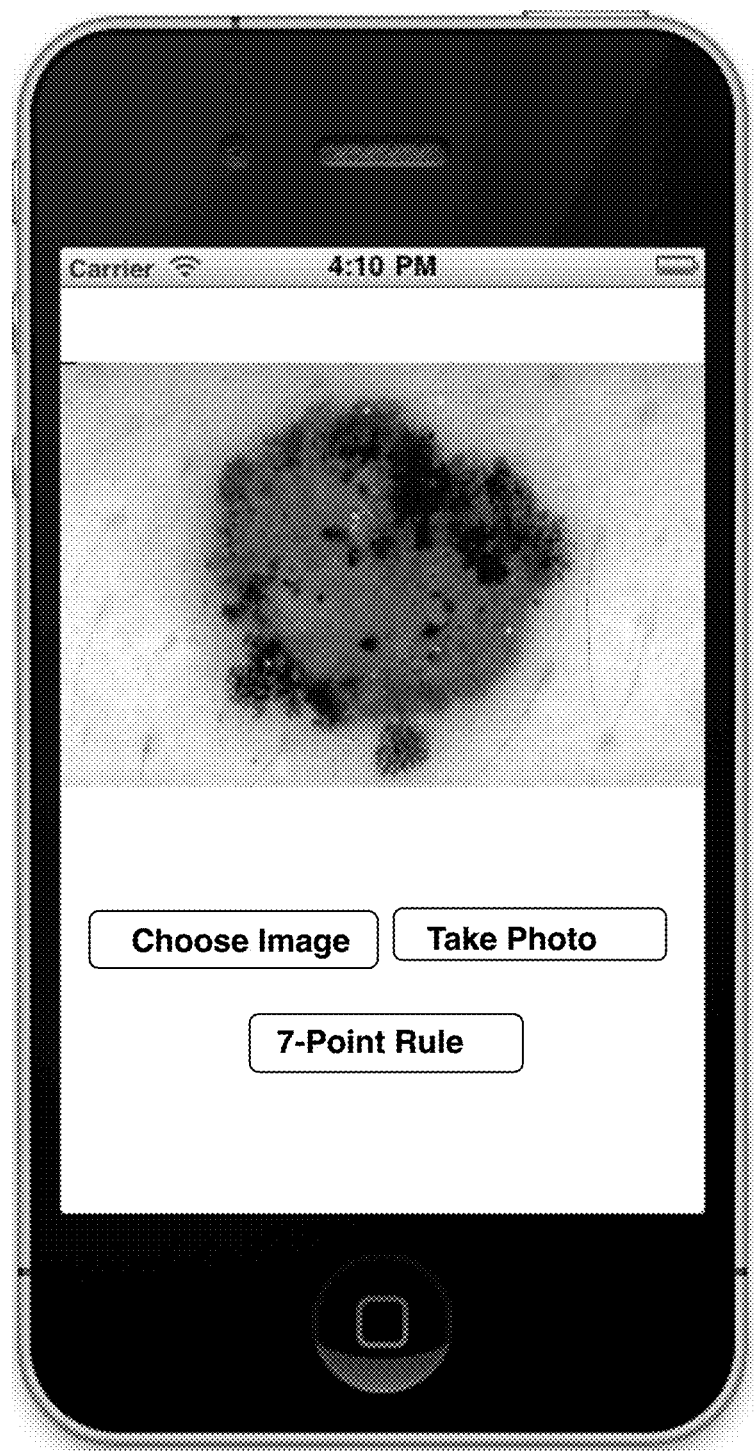
FIGS. 16A-16B depict the smartphone screen showing the image with menu choices (FIG. 16A) and the results and diagnosis after comparison with the 7-Points Criteria for detecting melanoma (FIG. 16B).
Figure 16B:
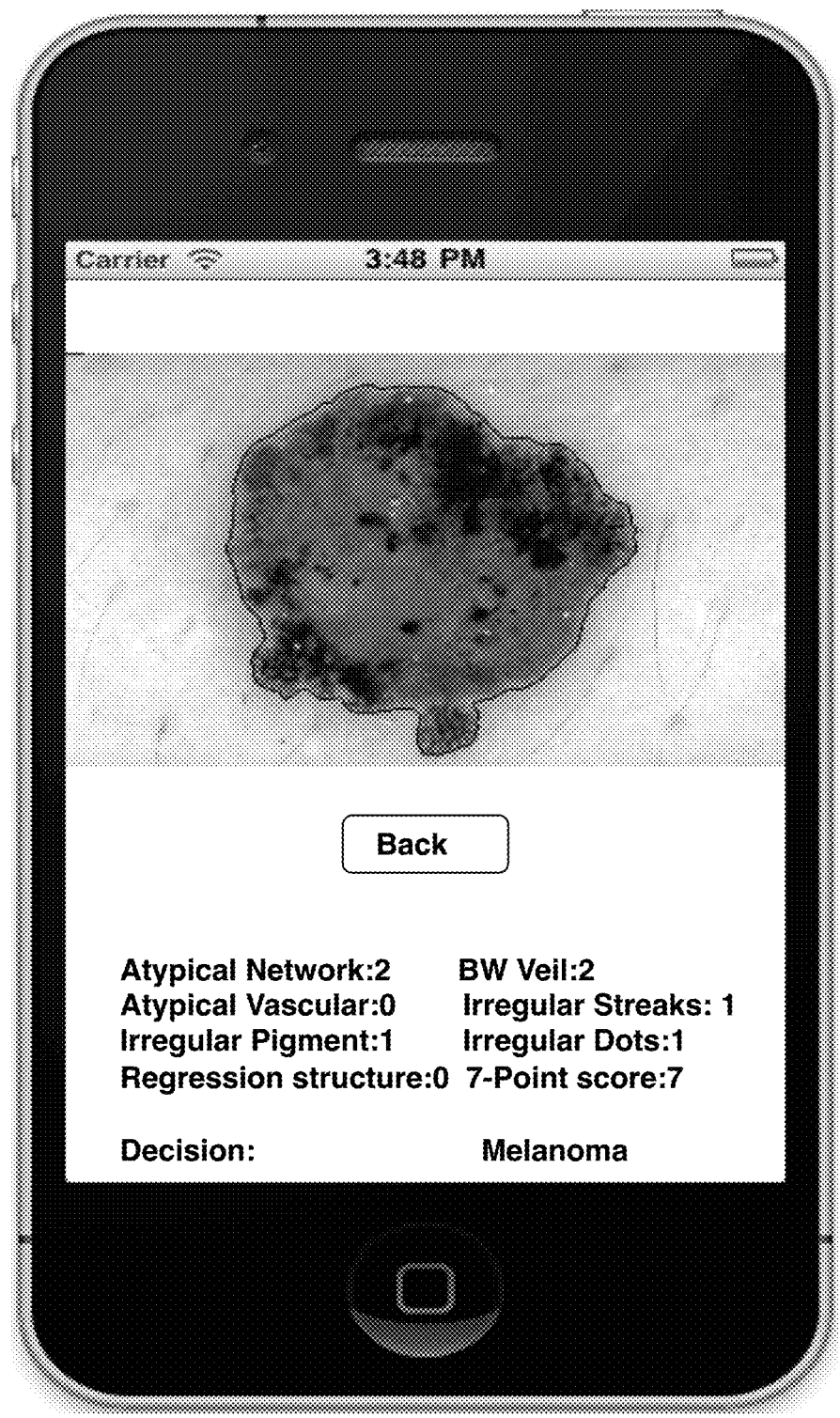

Generally, the end user can take an image of the skin lesion using the 5 megapixel built in camera with LED flash, or load the image from media library. The image is analyzed in quasi real time and the final result displayed on the screen. FIGS. 16A-16B depict the menu based application in use on an Apple® iPhone® device showing an image of a skin lesion acquired by the device with the options of choose image, take photo or 7-Point Rule. The next screen displays the scores for each of the 7 criteria, a total score and a diagnosis based on the same.

A 10-fold cross validation was performed on the set of 347 images to test the menu based application by comparing the classification accuracy of each criterion separately against the overall final classification by expert physicians (7). The dataset was divided into 10 folds, nine folds with 11 melanoma and 23 benign lesions and the remaining fold with 11 melanoma and 30 benign lesions. Of the 10 folds, nine were used for training and one was used for testing. 10 rounds of validation were performed where each fold was chosen for testing and the rest were for training, to get 10 experiments. The classification accuracy of each criterion was compared and the overall decision of the 7-point checklist with dermatology and histology.

Table 8 presents the sensitivity and specificity of the algorithm in classification of each of the 7-point checklist criterion. There was lower accuracy for the regression structures, because they are usually indistinguishable from the blue-whitish veil via dermoscopy (7). However, this is not an issue, as is it only necessary to obtain a minimum score of 3 to correctly detect a melanoma.

TABLE 8

Classification for all Criteria

|  | Sensitivity | Specificity |
|---|---|---|
| Atypical Pigment Network | 72.86% | 70.40% |
| Blue-Whitish Veil | 79.49% | 79.18% |
| Aypical Vascular Pattern | 75.00% | 69.66% |
| Irregular Streaks | 76.74% | 79.31% |
| Irregular Pigmentation | 69.47% | 74.21% |
| Irregular Dots and Globules | 74.05% | 74.54% |
| Regressive Structures | 64.18% | 67.86% |

In Table 9 the sensitivity and specificity of the algorithms is compared with the decision made by expert clinicians via dermoscopy. Table 10 presents the confusion matrix computed using the sum of ten confusion matrices from the ten test sets, given from the 10-fold cross validation. Another classification experiment using SVM also was performed, where the 7-point checklist was ignored and each skin lesion was directly classified as melanoma or benign. The feature vectors, feature selection scheme, and final ground truth (melanoma/benign) are the same as the classification using the automated 7-point checklist. Table 5 shows that classification accuracy is much lower when the 7-point checklist is ignored.

TABLE 9

Classification Accuracy

|  | Sensitivity | Specificity |
|---|---|---|
| 7-Point Checklist | 87.27% | 71.31% |
| Ignoring 7-Point Checklist | 74.78% | 70.69% |

TABLE 10

Confusion Matrix of the Automated Decision

| Confusion Matrix | | Predicted | |
|---|---|---|---|
|  |  | Melanoma | Benign |
| Dermoscopy | Melanoma | 96 | 14 |
|  | Benign | 68 | 169 |

Execution Time

The time needed for classification using the ISODATA segmentation algorithm (23) on the Apple® iPhone 3G® is compared with a typical desktop computer (2.26 GHz Intel® Core™ 2 Duo with 2 GB RAM, Intel Corporation). The average image size in the dataset is 552×825 pixels. The classification time includes time taken for feature extraction. Table 11 shows computation time in seconds for both platforms. It can be seen that the whole procedure takes under 10 sec to complete thereby demonstrating that the application is light enough to run on a smartphone which has limited computation power.

TABLE 11

Mean Computation Time

| Mean time (sec) | Apple ® iPhone 3G ® | Desktop Computer |
|---|---|---|
| Segmentation | 2.3910 | 0.1028 |
| Classification | 7.4710 | 0.2415 |

EXAMPLE 7

Implementation for Buruli Ulcers

Figure 17A:
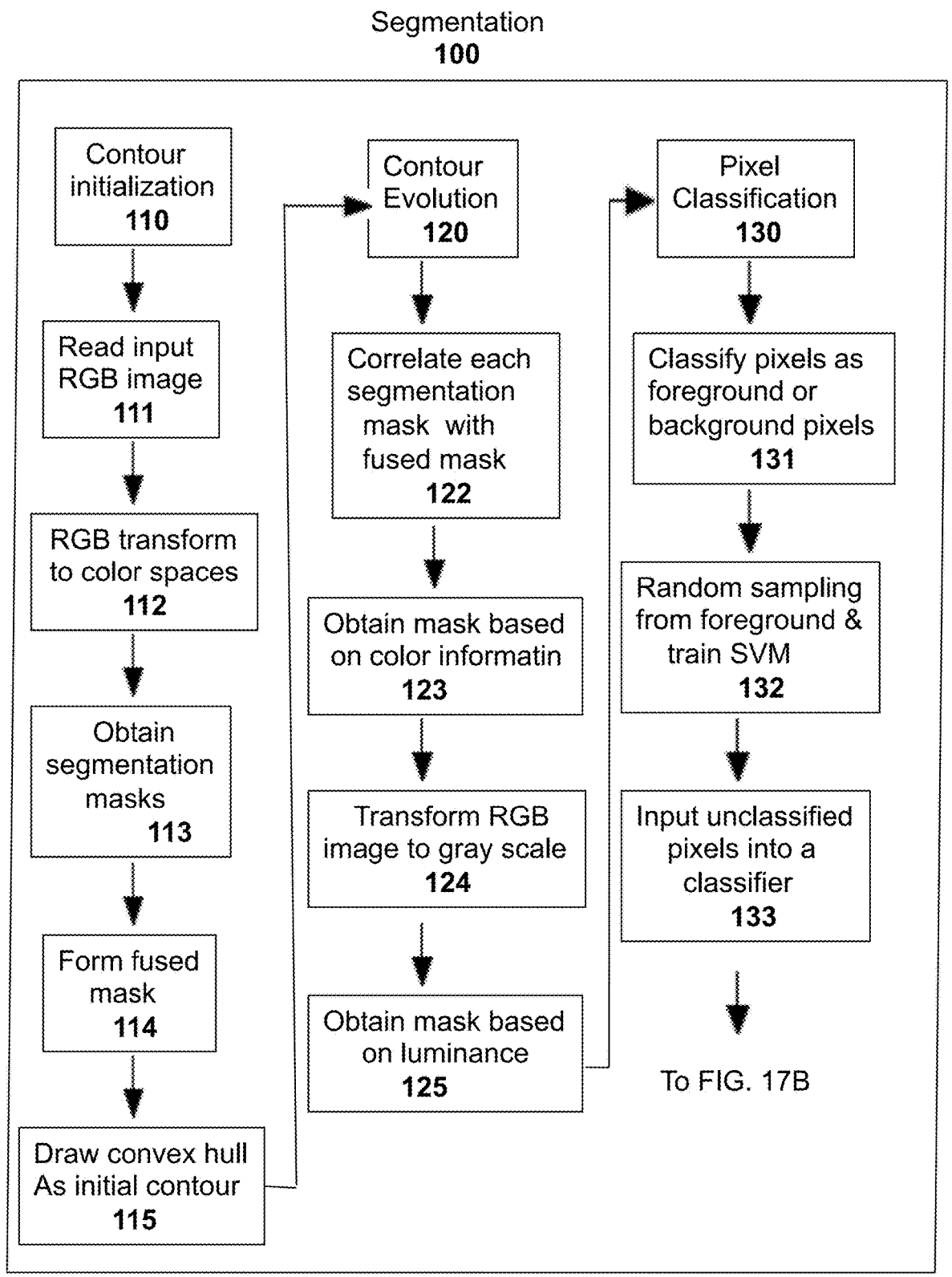
FIGS. 17A-17B depict a flowchart of the classification process in each of the algorithmic segmentation (FIG. 17A) and feature extraction and classification (FIG. 17B) modules.
Figure 17B:
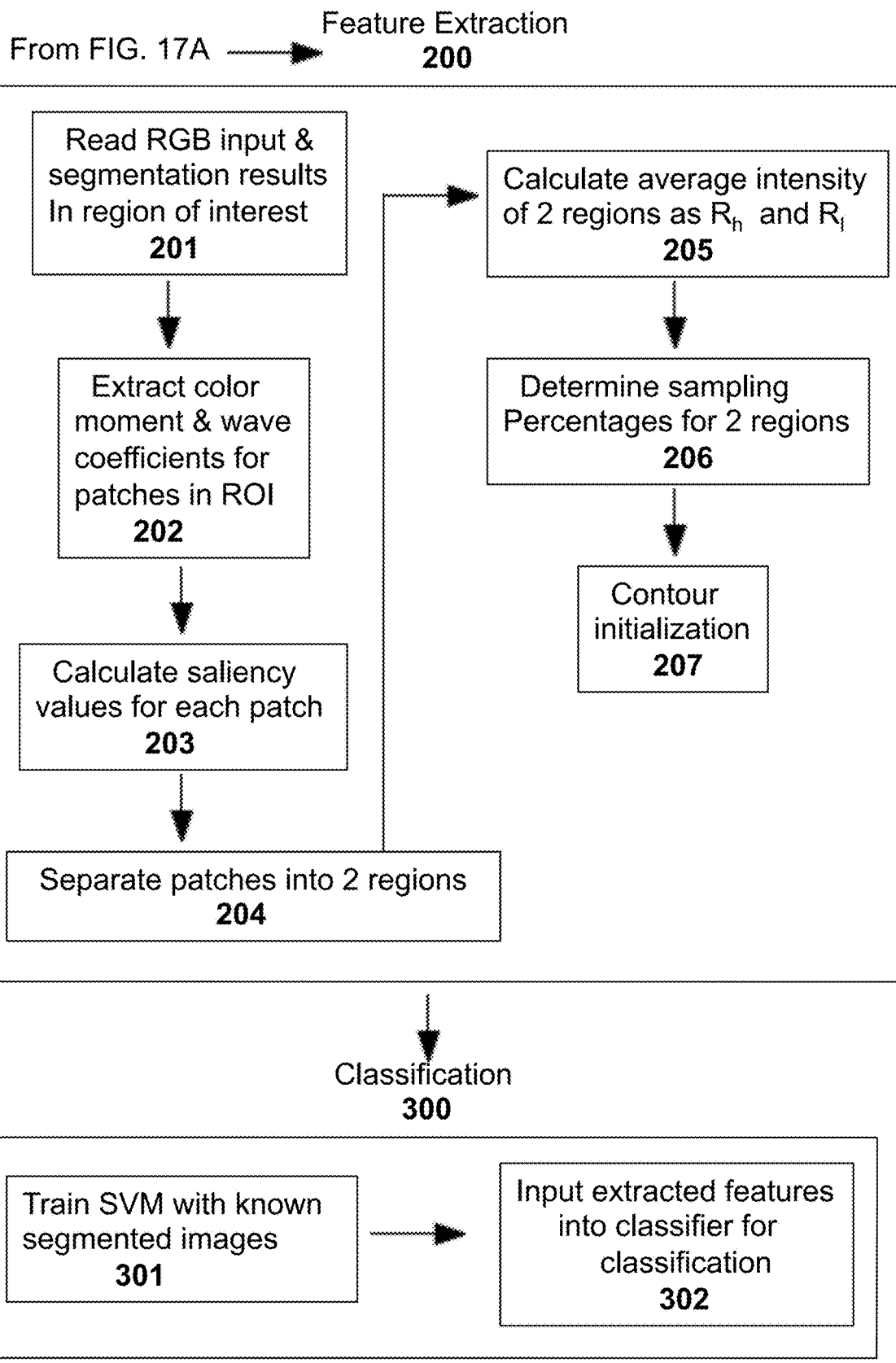

FIGS. 17A-17B are flowcharts depicting the algorithm steps in the segmentation, feature extraction and classification modules for identification/classification of an object of interest, for example, a Buruli ulcer, as in the below example, or a melanoma.

Segmentation

Both color and luminance are important characteristics for Buruli lesion segmentation. The key idea of the segmentation method simply starts by considering the common foreground and background obtained by the luminance and color components as lesion and skin, respectively, and then applying a supervised classifier to the remaining pixels is key. Segmentation 100 comprises the following steps.

First, contour initialization 110 comprises the following steps:

1) Read input RGB image at 111;

2) Transform RGB image to four other color spaces: La*b*, HSV, YCbCr, Lu*v* at 112;

3) Apply Otsu's thresholding method (1) to eight color channels: a*, b*, H, S, Cb, Cr, u*, v*, to obtain eight segmentation masks at 113.

4) Fuse these eight masks by a voting system to form a new mask at 114. For each pixel, if more than three masks agree to be foreground, then it is classified as a lesion pixel;

5) Draw a convex hull at 115 which covers the fused mask to be the initialized contour for the following steps.

Secondly, contour evolution 120 comprises the following steps:

1) For each segmentation mask obtained from the eight color channels, calculate the correlation coefficient with the fused mask at 121;

2) Apply the Chan-Vese Level Set segmentation method (2) for the color channel which has the largest correlation coefficient, to obtain a mask based on color information $M_c$ at 122.

Basically, in Chan-Vese, given an image $I \subset \Omega$, the region-based active contour model (37) assumes that image I is formed by two regions of approximately piecewise constant intensity c1 and c2 separated by a curve C, which minimizes the energy-based objective function:

$$F(c_1, c_2, C) = \mu \cdot \text{length}(C) + \lambda_1 \int_{inside(C)} \frac{1}{N} \sum_{i=1}^{N} |I_i(x) - c_{1,i}|^2 dx + \lambda_2 \int_{inside(C)} \frac{1}{N} \sum_{i=1}^{N} |I_i(x) - c_{2,i}|^2 dx \quad \text{(Eq. 10)}$$

where the parameters $\mu>0$ and $\lambda_1, \lambda_2>0$ are positive weights for the regularizing term and the fitting term, respectively. When applying the level set approach (38), the curve C can be represented as the zero level set $C(t)=\{(x)|\phi(t, x)=0\}$ of a higher dimensional level set function $\Phi(t, x)$. Then the energy function can be rewritten as $$E(\Phi, c_1, c_2) = \mu \cdot \int_\Omega \delta(\Phi)|\nabla\Phi| dx + \int_\Omega \frac{1}{N} \sum_{i=1}^{N} \lambda_1 |I_i(x) - c_{1,i}|^2 H(\Phi) dx + \int_\Omega \frac{1}{N} \sum_{i=1}^{N} \lambda_2 |I_i(x) - c_{2,i}|^2 (1 - H(\Phi)) dx, \quad \text{(Eq. 11)}$$

where H is the Heaviside function. The evolution of is governed by the following motion partial differential equation (PDE):

$$\frac{\partial \Phi}{\partial t} = \delta_s(\Phi) \left[ \mu \text{div}\left(\frac{\nabla\Phi}{|\nabla\Phi|}\right) - \frac{1}{N} \sum_{i=1}^{N} \lambda_1 |I_i(x) - c_{1,i}|^2 + \frac{1}{N} \sum_{i=1}^{N} \lambda_2 |I_i(x) - c_{2,i}|^2 \right] \quad \text{(Eq. 12)}$$

where $\delta(\Phi)$ is a regularized version of the Dirac delta function. The evolution can be solved using finite differences, by updating each $c_{1,i}$ and $c_{2,i}$ by the average of channel $I_i$ calculated inside (C) and outside (C).

3) Transform RGB image to gray scale image at 124; and

4) Apply the Chan-Vese Level Set segmentation method for the gray scale image, to obtain a mask based on luminance $M_l$ at 125.

Thirdly, pixel classification 130 comprises the following steps:

1) For each pixel at 131, if it belongs to the common foreground of $M_c$ and $M_l$, then it is classified as a foreground pixel or if it belongs to the common background of $M_c$ and $M_l$, then it is classified as a background pixel or it remains to be determined;

2) From the common background and foreground of $M_c$ and $M_l$, randomly sample 5000 pixels respectively, train a linear SVM using RGB and Lu*v* value at 132;

3) For each remaining pixel at 133, its RGB and Lu*v* value are used as input for the classifier to obtain a decision on this pixel being background or foreground.

Feature Extraction and Classification

As the first step, image sampling is a critical component when bag-of-features methods are used for image classification. The algorithms provided herein enable more patches from dermoscopic interest regions to be sampled based on saliency values. Given a patch, saliency (39) is defined as shown in Eqs. 5-7.

Feature extraction 200 comprises the following steps:

1) Read input for the RGB image and the segmentation result in the region of interest (ROI) at 201;

2) Extract color moment and wavelet coefficients for each patch inside ROI and assign a corresponding cluster number for each patch at 202;

3) Calculate saliency value according to Eqs. (5-7) for each patch inside ROI at 203;

4) Use k-means clustering to separate the lesion into two regions based on saliency values at 204;

5) Calculate the average intensity for separate regions respectively at 205. Region with higher intensity is denoted as $R_h$, and $R_l$ is for region with lower intensity;

6) Decide, at 206, sampling percentage for two separate regions by $$P_i = (\alpha \cdot A_i / \alpha \cdot A_l + A_h) \times 100\% \quad \text{(Eq. 13)},$$

where $P_h$ is the percentage of patches sampled from $R_h$, $A_h$ and $A_l$ are area of $R_h$, and $R_l$ respectively; $\alpha$ is a coefficient to control the percentage, here $\alpha$ is set to be 1.5; and 7) Randomly sample patches from $R_h$, and $R_l$ by corresponding sampling percentages and extract the bag-of-feature representation for each lesion at 207.

Classification 300 comprises the steps of:

1) Training for SVM using manually segmented images with known labels for Buruli and non-Buruli ulcers at 301; and 2) Extracted features are used as input at 302 for the classifier to obtain a decision whether or not the lesion is a Buruli lesion.

EXAMPLE 8

Obtention of Dermoscopic Images for Detection of Buruli Ulcers

Images were 24 bit full color with typical resolution of 4320×3240 pixels. Data were collected in endemic BU communities of Cote d'Ivoire and Ghana with the help of local collaborators to the project that included medical doctors, District Surveillance Officers, and community health workers, using a DermLite II Multi-Spectral device (www.dermlite.com) for image acquisition. The device could provide white light for crosspolarization epiluminescence imaging, blue light for surface coloration, yellow light for superficial vascularity, and red light for deeper coloration and vascularity, using 32 bright LEDs, eight per color. This device was attached to a Sony Cybershot DSC-W300 high-resolution camera, which provided a resolution of 13.5 MP. The study has received IRB approval from the Human Subjects Protection Committee at the University of Houston, as well as in Ghana and Ivory Coast, and all subjects and their parents gave written informed consent to the study in their native language.

EXAMPLE 9

Application of Segmentation Scheme to Suspected Buruli Lesions

A set of dermoscopic images of 26 suspected BU lesions were obtained as described herein. In the preprocessing step, images were first downsampled to 1080×810 pixels, and then processed with a 5×5 median filter and a Gaussian lowpass filter of the same size to remove extraneous artifacts and reduce the noise level. For postprocessing, morphological filtering was applied, and a distance transform (40) was used to make the borders smoother. As ground truth for the evaluation of the border detection error, for each image, manual segmentation was performed by a field expert in Africa just after acquisition. Three different metrics were used to quantify the boundary differences, namely XOR error rate (XER) (41), true detection rate (TDR), and false positive rate (FPR) (11), defined as follows, $$XER(A;M)=(A\ M)=M\ 100\%$$

$$TDR(A;M)=(A\backslash M)=M\ 100\%$$

$$FPR(A;M)=(A\backslash M)=M\ 100\%;\quad \text{(Eq. 14)}$$

where A denotes the area of automatic segmentation and M denotes the manual segmentation area obtained by the expert.

Figure 18A:
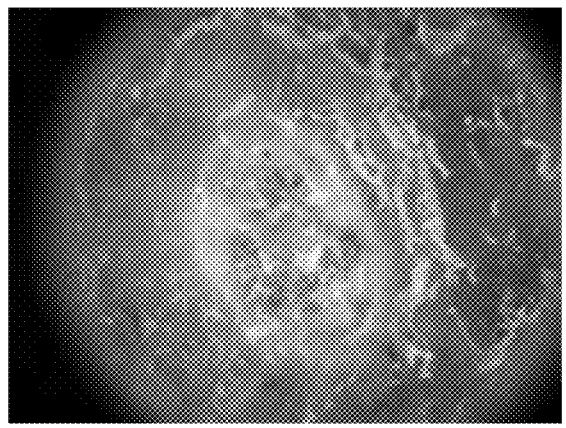
FIGS. 18A-18F are examples of Buruli ulcer (BU) segmentation showing the original BU image with manual segmentation (FIG. 18A), the initial mask by fusion (FIG. 18B), level set segmentation in color (FIG. 18C) and luminance (FIG. 18D) channels, segmentation after pixel classification (FIG. 18E), and the final segmentation result (FIG. 18F). The line(s) around the lesions show the result for automatic segmentation (FIGS. 18B-18E), the ground true from an expert dermatologist (FIG. 18A) or both (FIG. 18F).
Figure 18B:
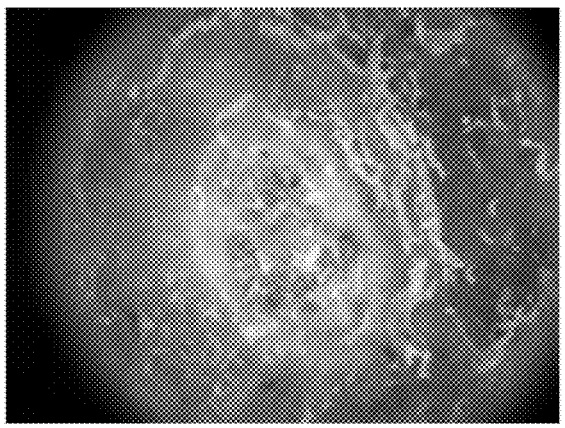
Figure 18C:
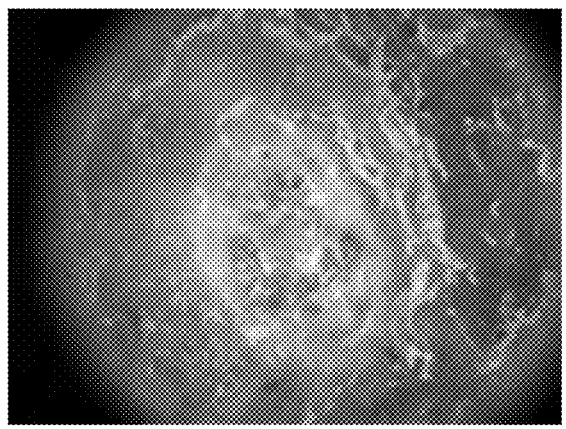
Figure 18D:
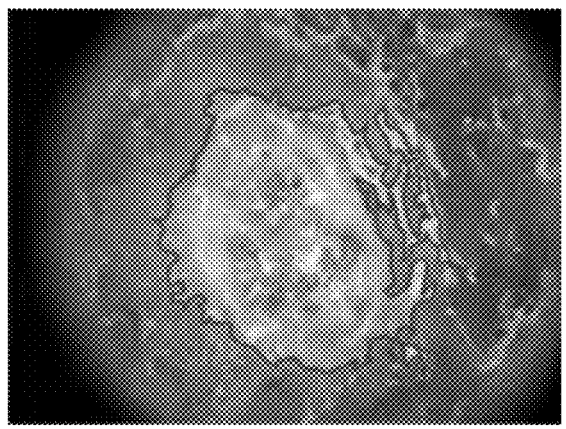
Figure 18E:
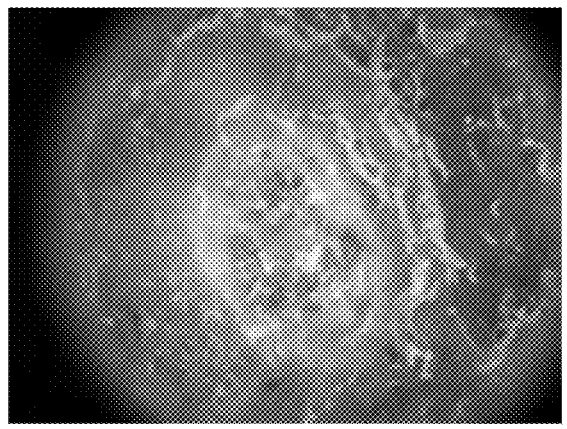
Figure 18F:
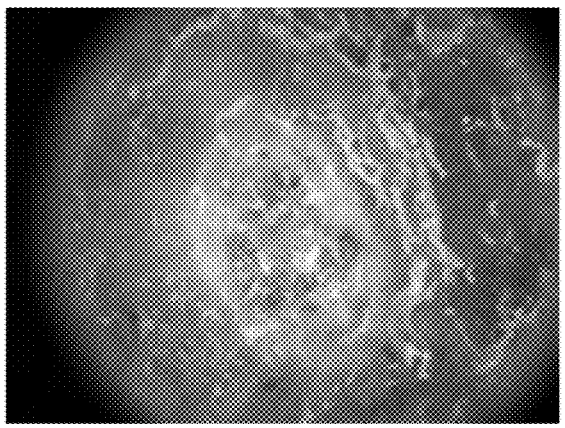
Figure 19A:
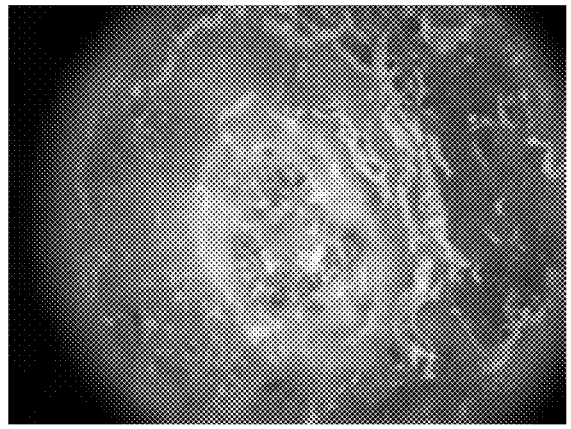
FIGS. 19A-19D depict different segmentation methods by AT (FIG. 19A), GVF (FIG. 19B), LS (FIG. 19C), and the instant segmentation method (FIG. 19D) where results from automatic segmentation and ground true from an expert dermatologist are included.
Figure 19B:
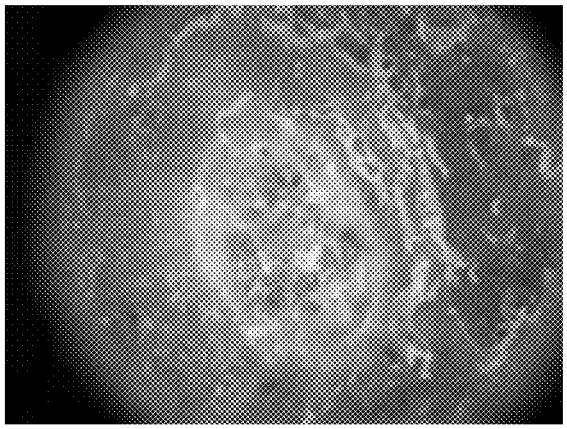
Figure 19C:
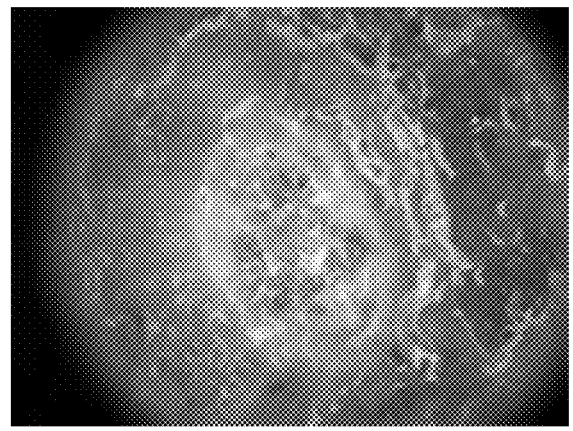
Figure 19D:
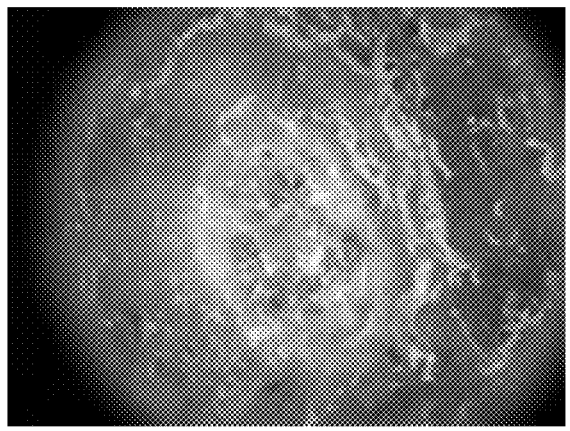
Figure 20A:
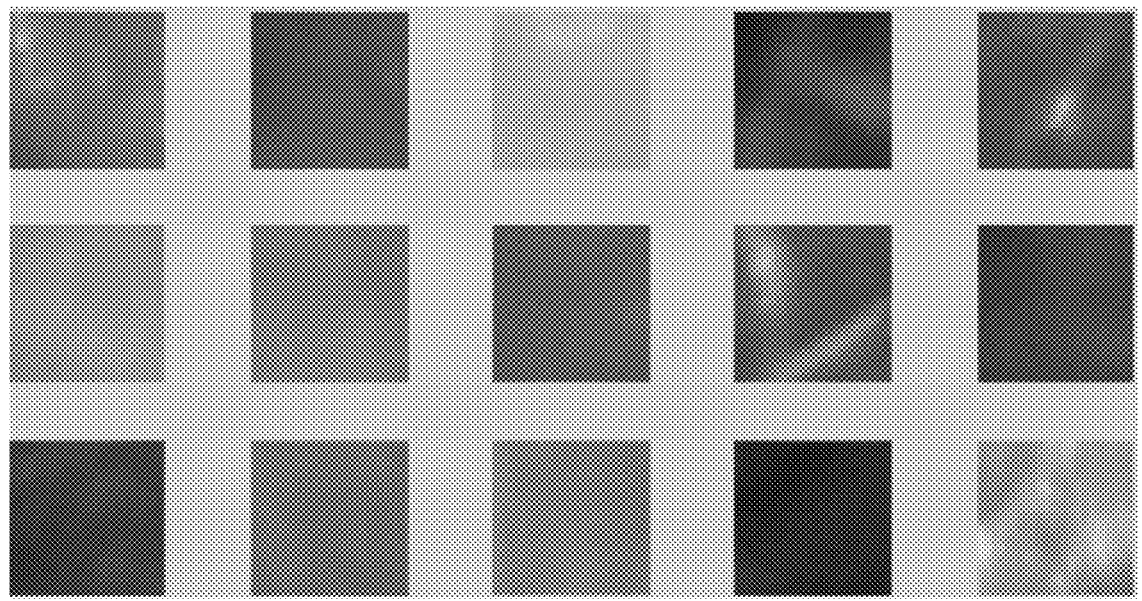
FIGS. 20A-20B are examples of image patterns closest to the two cluster centroids for Buruli lesions (FIG. 20A) and non-Buruli lesions (FIG. 20B).
Figure 20B:
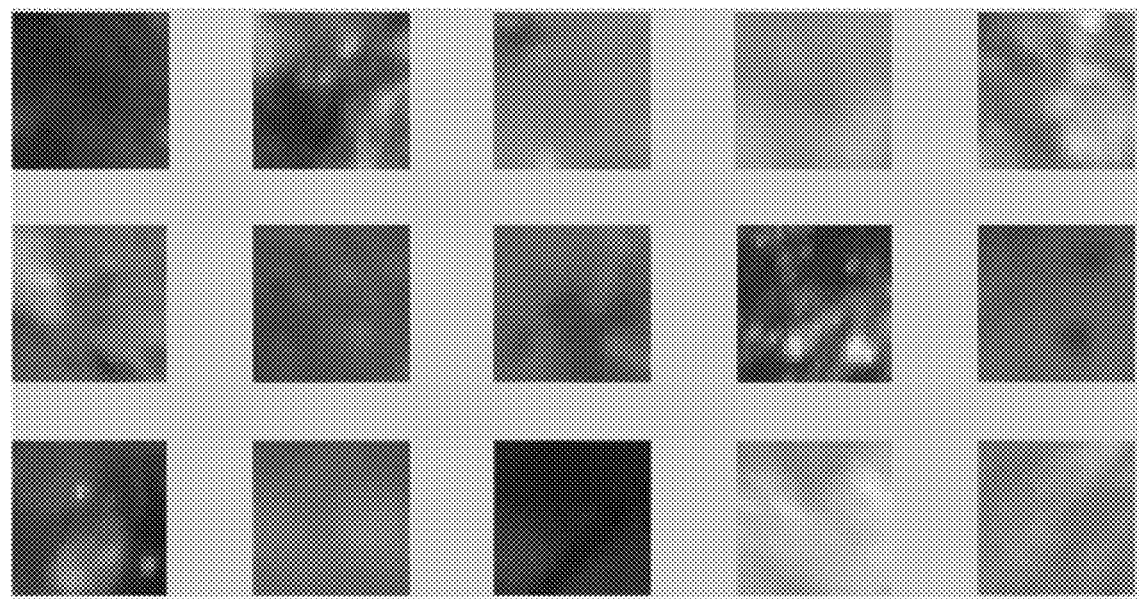

Images illustrating segmentation schemes are shown in FIGS. 18A-18D. Particularly, FIG. 18A shows the original lesion with the manual segmentation from the expert. The lesion consists of two main parts: central areas with variegated distinctive colors, and the surrounding erythematous areas which exhibit a smooth transition to normal skins. Also, the complex texture of normal skin caused by the infected skin makes the segmentation task more challenging. FIG. 18B shows the initial contour obtained by the fusion of thresholding segmentations from different color channels. The initial mask covers the most significant lesion colors. FIGS. 18C-18D present the segmentation results after contour evolution in the color and luminance components, respectively. It is obvious that the segmentation in the color channel is good at detecting the central area of a lesion with significant colors and misses the surrounding areas, while segmentation in the luminance channel is able to find the surrounding area, but always includes part of normal skin because of the smooth transition. The combination of color and luminance information by pixel classification is shown in FIG. 18E, while FIG. 18F presents the final segmentation result after morphological postprocessing. The latter is close to the expert's segmentation and detects both parts of the lesion successfully.

Comparison of Segmentation with Other Methods

The proposed segmentation method (based on Fusion and Classification, FC) was compared with three popular methods applied to skin lesion segmentation, namely adaptive thresholding (AT) (7), gradient vector flow (GVF) (8), and level set (LS) (11) segmentation. The initialization of contour for GVF and LS were both completed by the first step of the segmentation scheme. For GVF snake, the elasticity, rigidity, viscosity, and regularization parameters were $\alpha=0:05$, $\beta=0:01$, $\gamma=1$, and $k=0:6$, respectively. The maximum iteration number was 75. The LS method was processed in the L*a*b* color space, using parameters $\lambda_1=1$, $\lambda_2=1$; and $\mu=0:1$. The maximum number of iterations was 150. For this segmentation scheme, the same parameters as in the LS method were used for the contour evolution step, where 5000 foreground and 5000 background points were randomly sampled to train the classifier. The segmentation results obtained are shown in FIGS. 19A-19D. Among these approaches, the AT and LS methods were disturbed by the illumination of the surrounding normal skins, the GVF method converged to some noisy or spurious edge points, while the method described herein successfully detected both the central and surrounding areas of the lesion, resulting in an accurate border.

To quantify the performance of different segmentation methods, three different metrics, namely XER (41), TDR, and FPR (42) were used to measure the segmentation accuracy, as described (43). XER is computed as the number of pixels for which the automatic and manual borders disagree divided by the number of pixels in the manual border. It takes into account two types of errors: pixels classified as lesion by the expert that were not classified as such by the automatic segmentation and pixels classified as lesion by the automatic segmentation that were not classified as such by the expert, while the TDR method focuses on the former and the FPR focuses on the latter, respectively. Table 12 shows the segmentation performance of the different methods.

TABLE 12

Segmentation performance of different methods

| Methods | XER (std) | TDR (std) | FPR (std) |
| --- | --- | --- | --- |
| AT | 39.46 ± 26.14 | 84.84 ± 17.22 | 24.30 ± 00 |
| GVF | 24.01 ± 12.02 | 79.10 ± 12.97 | 4.17 ± 4.08 |
| LS | 26.54 ± 19.78 | 90.06 ± 8.44 | 16.60 ± 21.42 |
| FC | 19.25 ± 9.28 | 85.70 ± 9.86 | 5.15 ± 5.3 |

The LS method can achieve the highest TDR at the cost of a higher FPR, because it always includes lesions and part of normal skin. On the contrary, the GVF method performs the best in FPR at the cost of missing some actual lesion areas. Overall, the segmentation method provided herein can achieve the best XER while keeping a relatively high TDR and low FPR, and outperform other state-of-art segmentation methods in Buruli lesion images.

EXAMPLE 10

A Classifier for Automatic Detection of Buruli Lesions

A set of dermoscopic images of 58 lesions, in which 16 lesions were confirmed BU and 42 lesions were non-BU lesions were obtained, as described herein. Images were first downsampled to 1080 Å~810 pixels, then manual segmentation of all lesions was applied to ensure that evaluation of classification performance was not affected by possible discrepancies in the automated identification of the lesion boundaries. The default setup for bag-of-features was as follows: patches were sampled on a regular grid of 5 Å~5, with patch size 24 Å~24 pixels; color moments and wavelet coefficients were the patch descriptors; the codebook was generated by k-means clustering with a size of 50 codewords; an SVM classifier with RBF kernel was used for the final classification step. Leave-One-Out cross-validation was implemented to evaluate the performance of the method. Performance criteria included sensitivity, specificity, and balanced accuracy (BAC, i.e., average of sensitivity and specificity).

Codeword Representation

The idea of bag-of-features is that the large set of collected samples can be automatically arranged into sub-clusters sharing similar color and texture patterns. If some of these image patterns, i.e., cluster centroids, are distinctive, then the distributions of image patterns which represent the skin lesions can have strong discriminative power. In other words, if the common image patterns of BU images are distinguishable enough from those patterns of non-BU images, then the bag-of-features method can be a good way to classify BU and non-BU images.

FIGS. 18A-18B show the shared image patterns of BU and non-BU lesions, respectively. The collection of samples from BU and non-BU images is clustered into 15 subclasses, and the patches that are closest to the cluster centroids are displayed. Most of the BU image patterns are light in color and homogeneous in texture, corresponding to discolored and necrotic skin, while non-BU patterns are darker and have more complex textures.

Effect of Sampling Strategies

Figure 21A:
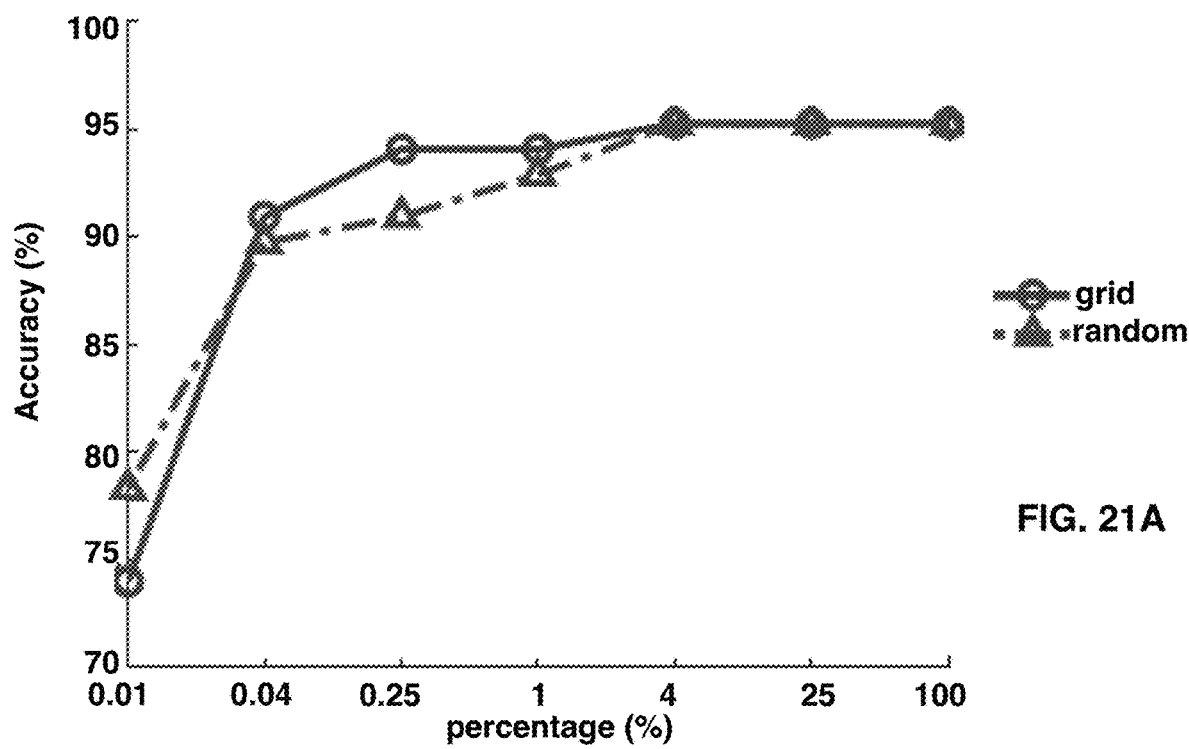
FIGS. 21A-21B illustrate the effect of sampling strategy on classification performance.

One of the main parameters governing classification accuracy and processing time is the number of patches sampled. Since lesions differ in size, the number of patches proportional to that lesion's area was chosen. Regular grid sampling and random sampling were applied with a patch size of 24×24 pixels, respectively. Grid sampling extracted patches on a regular grid with size chosen from the set {1, 2, 5, 10, 20, 50, 100}. Using a grid size g is equivalent to sampling approximately $(100/g^2)\%$ points from a lesion. Random sampling sampled patches randomly with the corresponding percentage. FIG. 21A shows the classification accuracy for different patch numbers. For both grid and random sampling, accuracy increases significantly as more patches are sampled, but it starts to converge when more than 4% of patches are sampled. Thus, only 4% of points need to be sampled from the lesion to achieve a maximum accuracy, but in substantially shorter time.

Figure 21B:
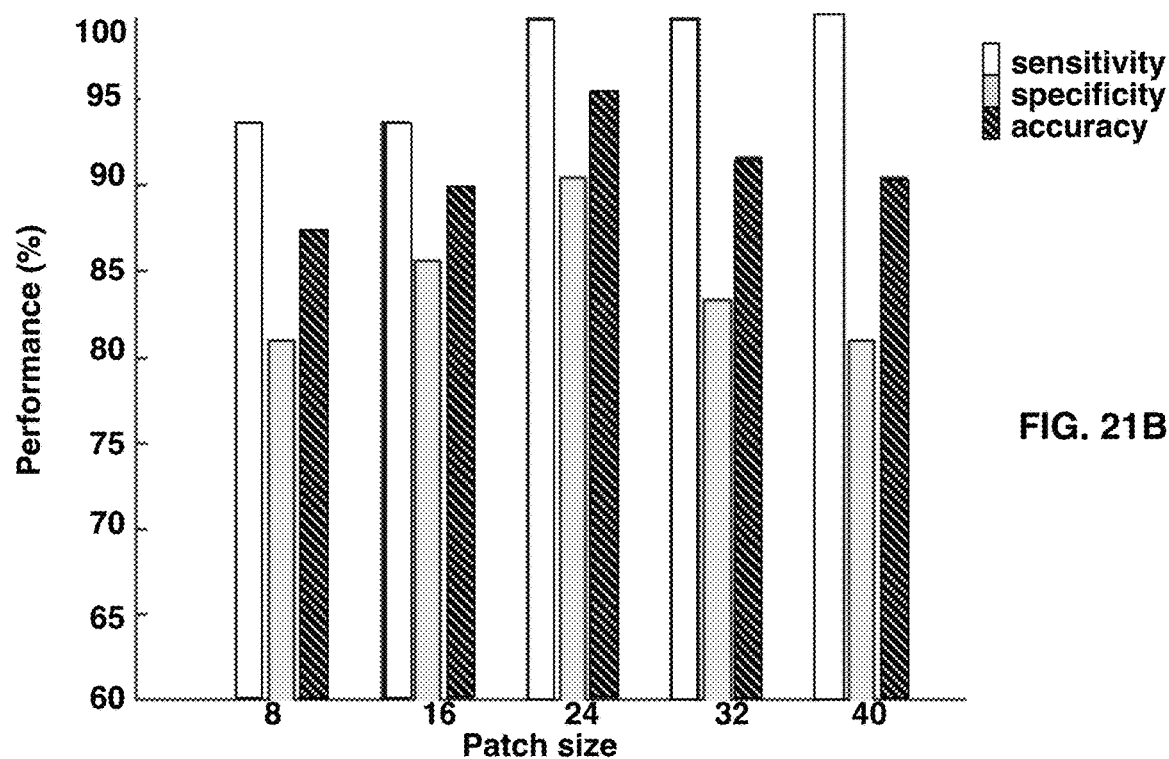

Patch size is another factor that can affect time and accuracy. Square patches of a size chosen from the set {8, 16, 24, 32, 40} on a grid of size 5×5 were extracted. FIG. 21B illustrates the impact of patch size on classification performance. A medium patch size of 24×24 pixels achieved the best performance in our experiments. Small patches can be processed very fast, but they capture less information, while large patches provide very good sensitivity. However, patches of very large size ignore some details of local characteristics and result in much higher computational complexity.

Effect of Patch Descriptors

In the bag-of-features method, patch descriptors are used to characterize image patches and to discover similar patterns across images. Different patch descriptors were tested, i.e., color moments and wavelet coefficients individually, as well as the combination of these two. Color moments captured color and shape information, and wavelet coefficients captured texture-related features. Table 13 shows that both single descriptors can achieve an accuracy around 80%, but that the combination can make a significant improvement to 95%, indicating that both color and texture are important to discriminate BU from non-BU images.

TABLE 13

Classification Performance of Different Patch Descriptors

| Descriptors | Sensitivity (%) | Specificity (%) | Accuracy (%) |
|---|---|---|---|
| Color | 87.50 | 69.05 | 78.27 |
| Texture | 87.50 | 83.33 | 85.41 |
| Combined | 100 | 90.48 | 95.24 |

Effect of Codebook Size

The number of codebook centers is another factor that affects the performance of bag-of-feature methods. Five codebook sizes were chosen from the set {10, 25, 50, 100, 200}. When the codebook size is small, patches are assembled into fewer groups, therefore the discriminative power is not strong. As patches are grouped into more clusters, the accuracy also increases; however, when the codebook size becomes too large, the dimension of the feature vector is also very large, so the overall performance decreases because of over-fitting.

Effect of SVM Kernels

The performance of different types of SVM kernels was investigated. Table 14 shows that the performance of the linear kernel is the worst, while the nonlinear RBF and the chi square kernels, which map the feature vector to a higher dimension feature space, can achieve better performance.

TABLE 14

Classification Performance of Different SVM Kernels

| Kernels | Sensitivity (%) | Specificity (%) | Accuracy (%) |
|---|---|---|---|
| Linear | 81.25 | 83.33 | 82.29 |
| RBF | 100 | 90.48 | 95.24 |
| Chi-square | 100 | 88.10 | 94.05 |

Depiction of Buruli Ulcer on a Smart Device

Figure 22A:
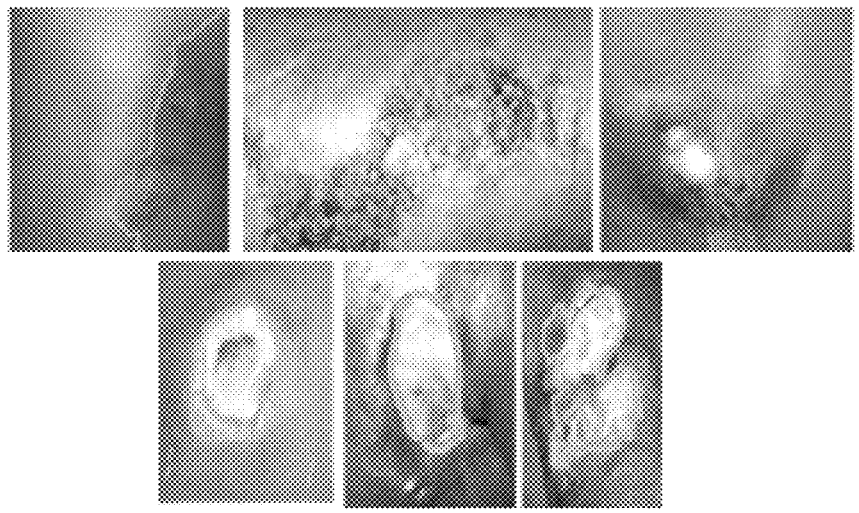
FIGS. 22A-22B illustrates ulcer variation of a Buruli ulcer from early to late stage (FIG. 22A) and demonstrates that the algorithms can distinguish between early and late stage ulcers (FIG. 22B).
Figure 22B:
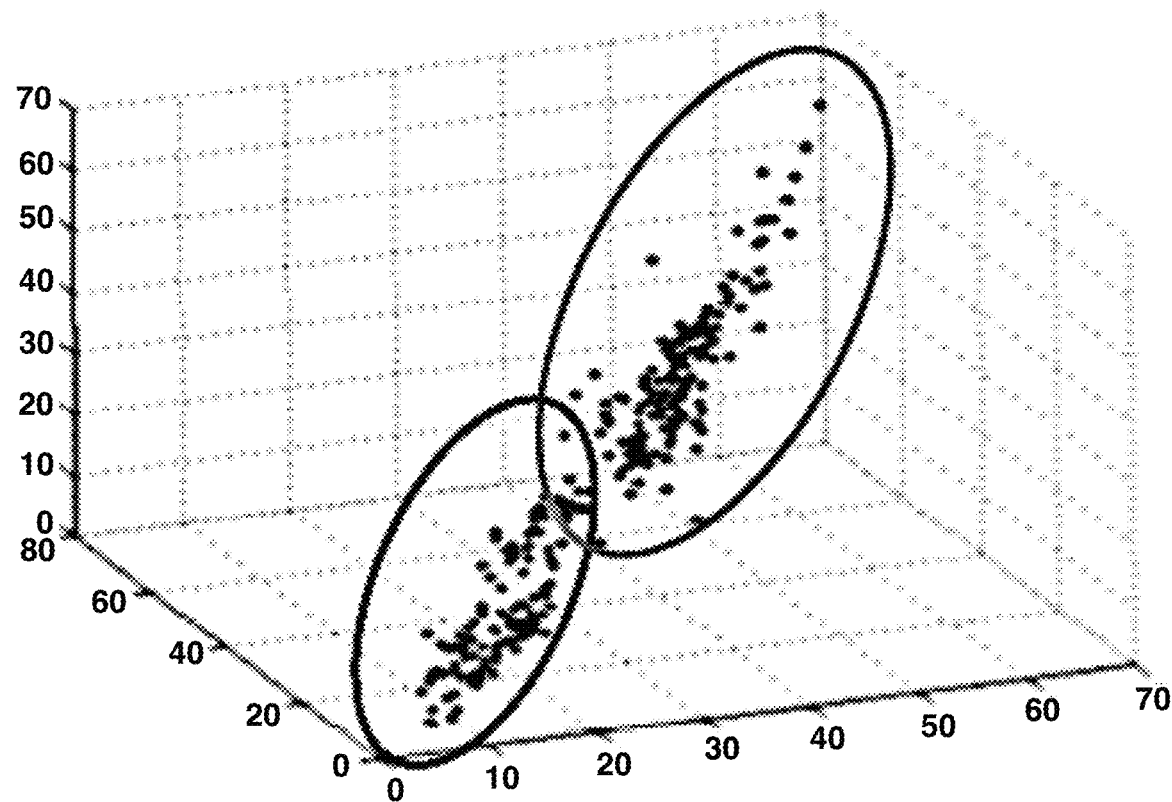

The algorithms described herein can detect and diagnose a Buruli ulcer in early or late stage (FIG. 22A). FIG. 22B illustrates the grouping of early and late lesions obtained from the bag-of-features and feature histograms created from wavelet and color moment features.

EXAMPLE 11

Implementation for Multispectral Imaging

Lights of different frequencies can penetrate different skin depths. For instance, blue light with a shorter wavelength of about 470 nm forms images of surface coloration, yellow light of about 580 nm forms images for superficial vascularity and red light with a longer wavelength of about 660 nm penetrates deeper and visualizes deeper vascularity. In this example, the algorithms are applied to the classification of a Buruli ulcer. However, this algorithmic process is applicable to the identification and classification of other objects of interest, as described herein.

Architecture Overview

Figure 23:
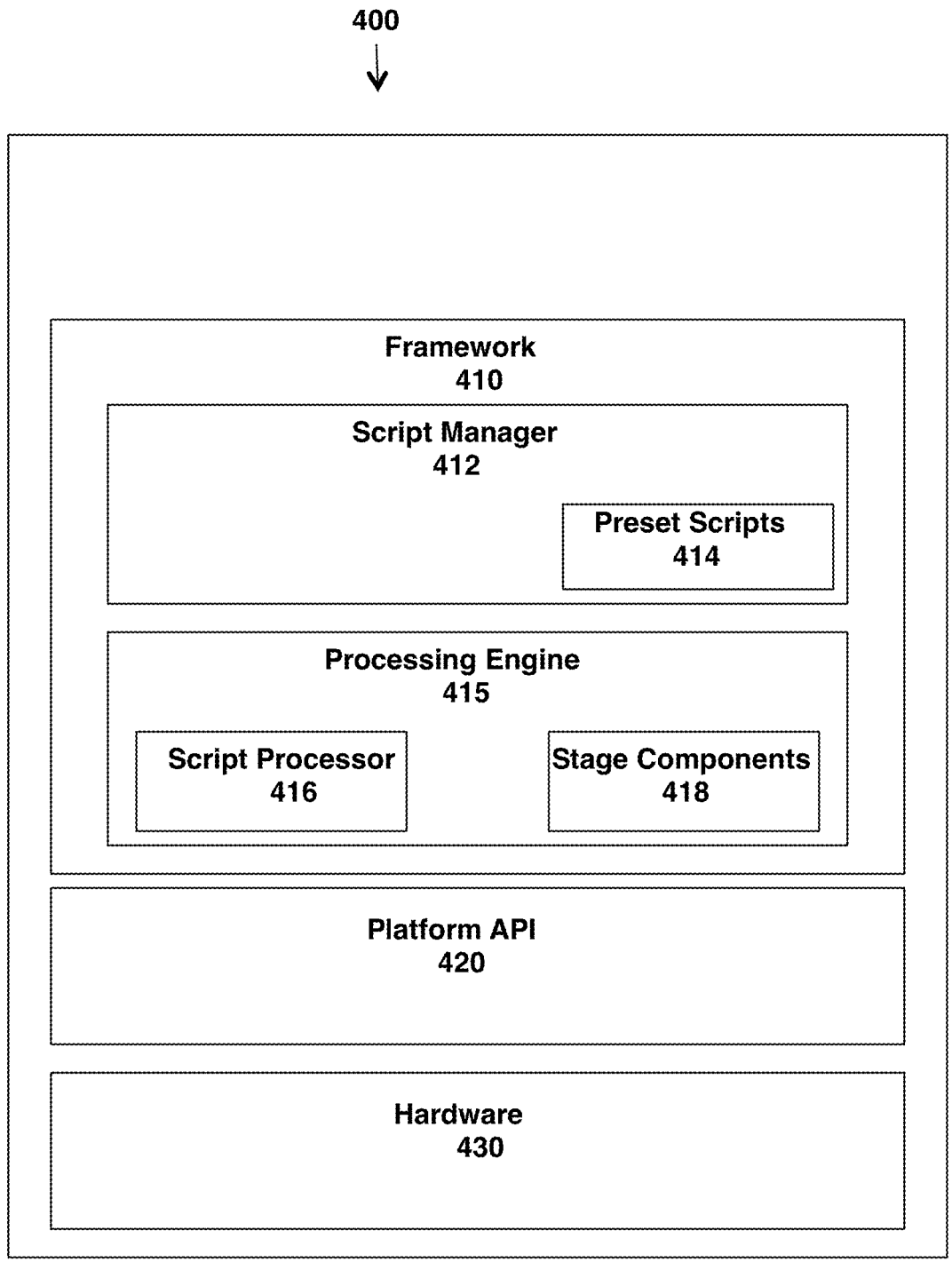
FIG. 23 depicts the architecture for the multispectral imaging process.

The architecture 400 (FIG. 23) for the extension and control of the processing chain for multispectral images comprises a framework 410 having the primary tiers Script Manager 412 and Processing Engine 415 on an application programmer interface (API) platform 420 with associated hardware 430. The Script Manager tier handles the configuration and execution of the DSL scripts 414 that represent process chains. A process chain encapsulates the particular execution steps required for analysis of a category of skin lesion, as described herein. Processing chains, comprising one or more process stages, are described using a DSL designed for skin-lesion image processing. Each process stage may consist of one or more image processing modules (IMPs), which are typically implemented in the C or C++ programming language. The DSL exposes these processes in a manner that allows an end user to chain IMPs, either in serial or parallel, without having intimate knowledge of the IMP implementation or the programming language that was used to develop it.

The following is an example of a DSL implementation of the process chain:

```
Define_chain "classifier_rule_chain", image do
    artificat_removal
    hair_removal
    segmentations = in_parallel do
        fuzzy_c_means
        active_contours
    end
    segmentation = score_and_return segmentations
    with segmentation do
        extract_features
        classify_lesion
    end
end
```

Process chains are completely configurable with only changes to the DSL scripts, allowing users to quickly try several analysis approaches. IMPs can be added to the system by developers who have minimal knowledge of the overall framework. Process chains can include other chains, so that it is possible for example to run a skin cancer and a Buruli analysis on the same lesion at the same time The processing engine 415 comprises a script processor 416 and stage components 418. The processing engine executes the preset scripts in the script processor, returning the results to the script manager. The processing engine is responsible for reading and interpreting the script, managing the script as it runs and instantiating process steps, as required. Also, the processing engine interfaces with the underlying operating system's API 420 to facilitate the use of native processing capabilities, including process and memory management and user interaction.

Segmentation

Segmentation is performed as per process 100 described herein.

Feature Extraction

In feature extraction color moments for white light images, histogram of intensities for multispectral images, and texture properties for both from an object of interest, such as, but not limited to, a Buruli ulcer are extracted. Extracted features are used as input to support vector machine (SVM), which outputs the classification, such as whether the lesion is Buruli or not or whether the lesion is malignant or not.

Figure 24:
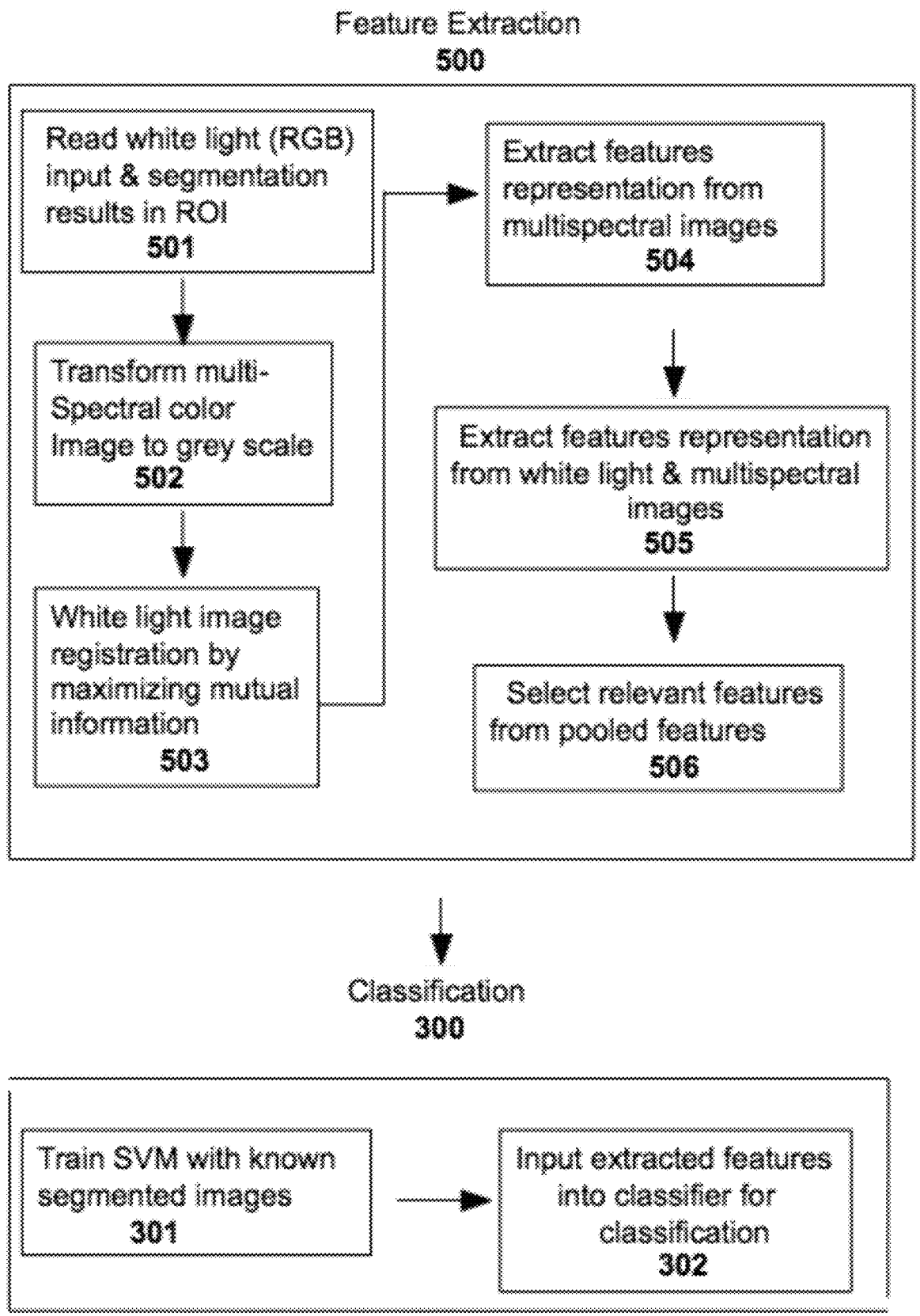
FIG. 24 depicts a flowchart of the classification process in algorithmic feature extraction and classification modules for multispectral images.

Feature extraction 500 (FIG. 24) comprises the steps of:

1) Read at 501 the input white light image (RGB) and segmentation result (region of interest (ROI));

2) Read at 502 the input multispectral images of blue, yellow, and red channel, and transform to gray scale images;

3) Use white light image as a reference image, do image registration for multispectral
images by maximizing mutual information at 503;

4) Extract bag-of-feature representation within ROI from the white light image with wavelet coefficients and color moment, respectively at 504;

5) Extract bag-of-feature representation within ROI from multispectral images with wavelet coefficients and histograms, respectively, at 505; and 6) Pool features from the white light image and multispectral images together, and perform feature selection to choose relevant features at 506.

Classification

Classification (FIG. 24) is performed as per process 300 described herein.

EXAMPLE 11

Optical Skin Model

Skin tissues have different absorption and scattering properties when lights of different frequencies passing through different skin layers. The attenuation coefficients of epidermis and dermis are related to three parameters, e.g. the volume fractions of melanin, blood, and oxygenation respectively. Provided herein is an implementation of an algorithm for multispectral image classification based on the following optical skin models.

$$I_{det}(\lambda) * I_{calibration}(\lambda) = S * A_{epi}(\lambda)^2 * A_{dermis}(\lambda) \quad (\text{eq. 15})$$

where $\lambda$ is the wavelength, $I_{det}(\lambda)$ is the detected intensity at each pixel for each wavelength, $I_{calibration}(\lambda)$ is the calibration factor, $A_{epi}(\lambda)$ is the attenuation of the light intensity after passing through the epidermis, and $A_{dermis}(\lambda)$ is the attenuation of light intensity passing through dermis.

Here, $A_{epi}(\lambda)$ is related to the volume fraction of melanin. It can be determined by, $$A_{epi}(\lambda) = \exp[-\mu_{a(epi)}(\lambda) t] \quad (\text{eq. 16})$$

where t is the thickness of epidermis, which can be considered to be constant as 0.6 mm, and $$\mu_{a(epi)}(\lambda) = V_{mel}\mu_{a(mel)}(\lambda) + (1 - V_{mel})\mu_{a(skin)}(\lambda) \quad (\text{eq. 17})$$

where $\mu_{a(mel)}$ is the melanin absorption coefficient, and $\mu a(skin)$ $(\lambda)$ is the absorption coefficient of normal skin. These two coefficients are known parameters. The remaining variable is the volume fraction of melanin in the epidermis $V_{mel}$.

In addition, $A_{dermis}(\lambda)$ is related to volume fraction of blood in the tissue and the percent of that blood that is oxygenated. It can be determined by, $$A_{dermis}(\lambda) = 1.06 - 1.45[\mu_{a(dermis)}(\lambda)/\mu'_s(\lambda)]^{0.35} \quad (\text{eq. 18})$$

where $\mu_s'(\lambda)$ is the reduced scattering coefficient of the dermis, which is determined by the wavelength and $$\mu_{a(dermis)}(\lambda) = V_{blood}\mu_{a(blood)}(\lambda) + (1 - V_{blood})\mu_{a(skin)}(\lambda) \quad (\text{eq. 19})$$

where $V_{blood}$ is the volume fraction of blood in the dermis layer and, $$\mu_{a(blood)}(\lambda) = V_{oxy}\mu_{a(oxy)}(\lambda) + (1 - V_{oxy})\mu_{a(deoxy)}(\lambda) \quad (\text{eq. 20})$$

where $V_{oxy}$ is the fraction of blood that is oxygenated, $\mu_{a(oxy)}(\lambda)$ and $\mu_{a(deoxy)}(\lambda)$ are the absorption coefficients of $HbO_2$ and Hb respectively. So the three remaining variables are: $V_{mel}$, $V_{blood}$, and $V_{oxy}$. By inserting Eq. 16-20 into Eq. 15, and using intensities obtained from three different channels, three unknown physiological parameters $V_{mel}$, $V_{blood}$, and $V_{oxy}$ can be solved.

Segmentation

Segmentation is performed as per process 100 described herein.

Feature Extraction

Figure 25:
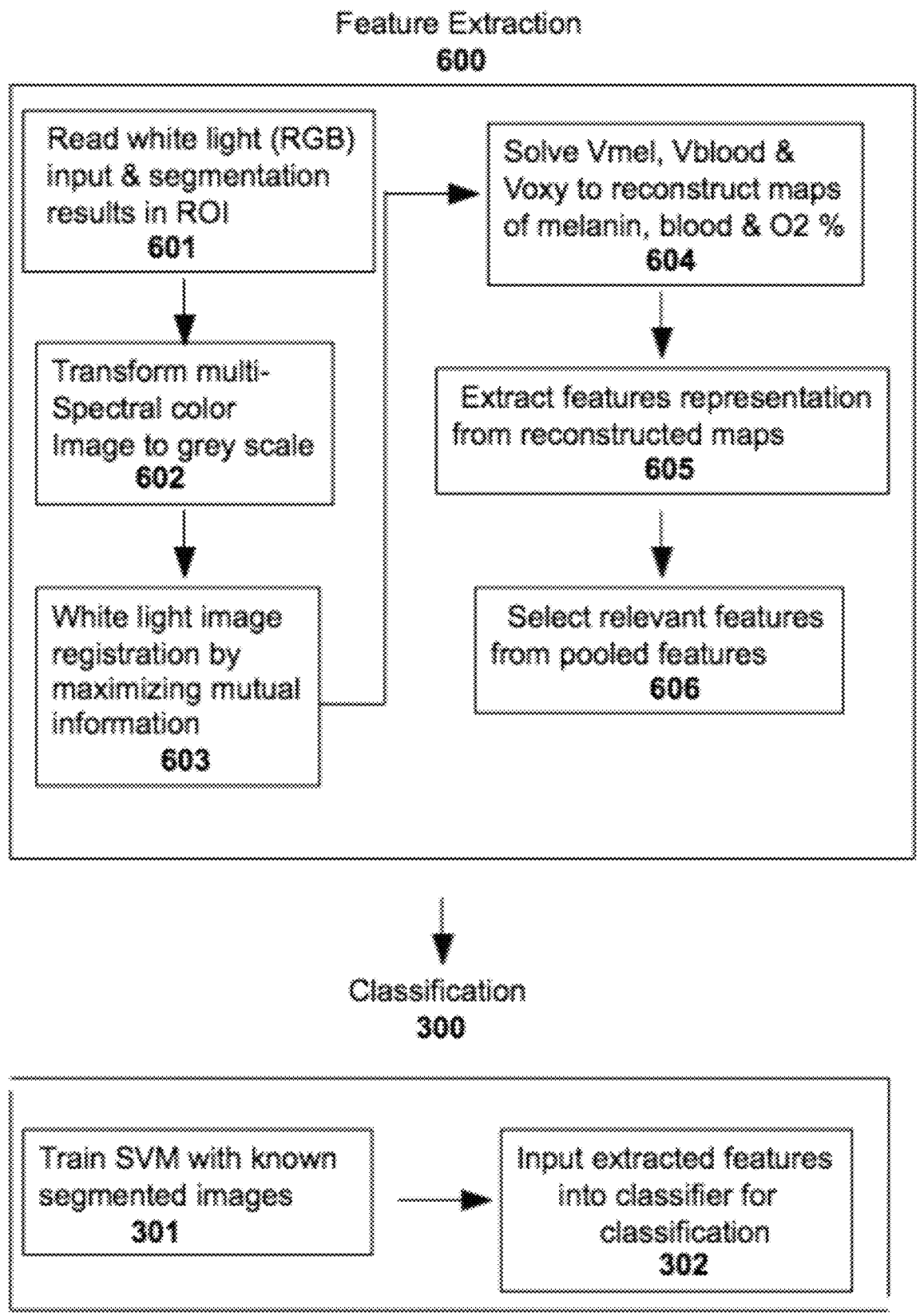
FIG. 25 depicts a flowchart of the classification process in algorithmic feature extraction and classification modules for an optical skin model.

Feature extraction 700 (FIG. 25) comprises the steps of:

1) Read at 601 input white light image (RGB) and segmentation result (region of interest (ROI));

2) Read at 602 input multispectral images of blue, yellow, and red channel, and transform to gray scale images;

3) Use white light image as a reference image, do image registration for multispectral
images by maximizing mutual information at 603;

4) For each pixel within ROI, solve $V_{mel}$, $V_{blood}$, and $V_{oxy}$ by Eqs. 5-7 to reconstruct maps of melanin, blood, and oxygenating percentage at 604;

5) Extract bag-of-feature representation within ROI from the reconstructed maps with
wavelet coefficients and histograms, respectively, at 605; and 6) Pool features from reconstructed images and perform feature selection to choose relevant features at 606.

Classification

Classification (FIG. 25) is performed as per process 300 described herein.

The following references are cited herein.
1. Jemal et al. CA: A cancer Journal for Clinicians, 60(5): 277, 2010.
2. Ganster et al. IEEE Transactions on Medical Imaging, 20(3):233-239, 2001.
3. Csurka et al. Workshop on Statistical Learning in Computer Vision, ECCV, 22(1), 2004.
4. Morris and Guilak, Pervasive Computing, IEEE, 8(2):57-61, April-June 2009.
5. Logan et al. American Journal of Hypertension, 20(9): 942-8, 2007.
6. Hicks et al. Wireless Health 2010, WH'10:34-43, New York, N.Y., USA 2010.
7. Argenziano et al. Dermoscopy: A Tutorial, Vol. 12, February 2000.
8. Argenziano et al. J Am Acad Dermatol, 48(5):679-93, 2003.
9. Situ et al. Annual International Conference of the IEEE Engineering in Medicine and Biology Society, 1:3110, 2008.
10. Yang et al. IEEE Conference on Computer Vision and Pattern Recognition (CVPR), IEEE, 2009.
11. Zhou et al. Biomedical Imaging: From Nano to Macro, 2009, IEEE:1318-1321, 2009.
12. Lowe, D. G., International Journal of Computer Vision, 60(2):91-110, 2004.
13. Frangi et al. Medical Image Computing and Computer-Assisted Intervention-MICCAI 98:130, 1998.
14. Zhou et al. Biomedical Imaging: From Nano to Macro, 2008, $5^{th}$ IEEE:1318-800-803, 2008.
15. Rubinov, M. and Sporns, O., Neuroimage, 2009.
16. Cucchiara, R. and Grana, C., Knowledge-Based Intelligent Information Engineering Systems and Allied Technologies: Kes 2002: 166, 2002.
17. Sadeghi et al. Proceedings of SPIE, 7623:762312, 2010.
18. Situ et al. Annual International Conference of the IEEE Engineering in Medicine and Biology Society, 2010.
19. Vapnik, V., Statistical Learning Theory, Vol. 2, Wiley New York, 1998.
20. Lanckriet et al. Journal of Machine Learning Research, 5:27-72, 2004.
21. Huang et al. Acoustics, Speech and Signal Processing, IEEE Transactions on, 27:13-18, February 1979.
22. Ridler, T. W. and Calvard, S., IEEE Transactions on Systems, Man and Cybernetics, SMC-8:630-632, 1978.
23. Dunn, J. C., Journal of Cybernetics, 3:32-57, 1973.
24. Bezdek, J. C., Pattern Recognition with Fuzzy Objective Function Algorithms, Plenum Press, 1981.
25. Chan and Vese, IEEE Transaction on Image Processing, 10:266-277, 2001.
26. Shapiro, L. G. and Stockman, G. C., Computer Vision, Prentice Hall, 2001.
27. Menzies et al. Arch Dermatol, 132(10):1178-1182, 1996.
28. Argenziano et al. Arch Dermatol, 134:1563-70, 1998.
29. Elbaum et al. Jour of American Academy of Dermatology, 44(2):207-218, 2001.
30. Stollnitz et al. IEEE Computer Graphics and Applications, 15:76-84, 1995.
31. Hartigan, J. A. and Wong, M. A., Applied Statistics, 28:100-108, 1979.
32. Xu et al. Image and Vision Computing, 17:65-74, 1999.
33. Fawcett, T., Pattern Recognition Letters, 27(8):861-874, 2006.
34. van de Sande et al. IEEE Transactions on Pattern Analysis and Machine Intelligence, 32(9):1582-96, 2010.
35. Ojala et al. IEEE Transactions on Pattern Analysis and Machine Intelligence, 24:971-987, 2002.
36. Stanley et al. Skin Research and Technology, 13(1):62-72, 2007.
37. Chan et al. Journal of Visual Communication and Image Representation, 11(2):130-141, 2000.
38. Osher, S. and Sethian, J. A. Journal of Computational Physics, 79(1):12-49, 1988.
39. Parikh et al. Computer Vision ECCV 2008, pp. 446-459, 2008.
40. Sanniti di Baja, G. and Svensson, S. In Pattern Recognition, 2000. Proceedings. $15^{th}$ International Conference on, Vol 2:1030-1033, 2000.
41. Celebi et al. Computerized Medical Imaging and Graphics, 33(2):148-153, 2009.
42. Silveira et al. IEEE Journal of Selected Topics in Signal Processing, pages 35-45, 2009.
43. C. Drummond, C. and Butler, J. R. Emerg Infect Dis, 10.
44. Fan et al. Visual categorization with bags of keypoints. In workshop on Statistical Learning in Computer Vision, ECCV, Vol. 22, 2004.
45. Leung, T. and Malik, J. International Journal of Computer Vision, 43:29-44, 2001.
46. Jurie et al. Proc. European Conference on Computer Vision, pgs. 490-503,2006.
47. Gool et al. Computer Vision and Image Understanding, 94:3-27, 2004.
48. Situ et al. Biomedical Imaging: From Nano to Macro, 2011 IEEE International Symposium, pgs. 109-112, Mar. 30-Apr. 2, 2011.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A digital processor-implemented method for performing simultaneous analyses of an object on the skin of an animal body, comprising the processor executable steps of:
   imaging the object with a hand-held imaging device;
   performing simultaneously on the image of the object an analysis of an object of interest as a skin cancer and an analysis of the object as an ulcer; and
   classifying the object as a skin cancer or as an ulcer or as neither from results obtained from the skin cancer analysis and the ulcer analysis,
   wherein the step of performing simultaneously the analysis of the object of interest comprises the processor executable steps of:
   segmenting the imaged object to detect a border of the object; and
   extracting features from the segmented object image,
   wherein the processor executable step of segmenting comprises:

determining an initial contour of the imaged object;
classifying pixels as contained within the initial contour as foreground, as contained without the initial contour as background or as remaining pixels if they are not classified as foreground pixels or background pixels; and
applying a supervised classifier to the remaining pixels for classification as foreground or background,
wherein the processor executable step of extracting comprises:
dividing the segmented object image into regions based on saliency values calculated for at least one patch within the segmented object;
dividing the regions into two regions of higher or lower intensity based on average intensity values thereof; and
extracting feature representations from a sampling of patches within the intensity regions based on sampling percentages determined for the regions, and
wherein the analysis is for an ulcer and is performed simultaneously with steps for classifying the skin cancer, said processor executable step of classifying comprising:
inputting the extracted feature representations from the object imaged on the skin into a support vector machine trained with manually segmented objects from an ulcer; and
classifying the object as an ulcer or as not an ulcer based on a comparison of the inputted extracted features with those in the support vector machine trained on a known ulcer.

2. The method of claim 1, further comprising: displaying the results as each result occurs.

3. The method of claim 1, wherein the analysis is for a skin cancer, said processor executable step of classifying comprising:
inputting the extracted feature representations from the object imaged on the skin into a support vector machine trained with manually segmented objects from a skin cancer; and
classifying the object as a skin cancer or as not a skin cancer based on a comparison of the inputted extracted features with those in the support vector machine trained on a known skin cancer.

4. The method of claim 3, wherein the skin cancer is a melanoma.

5. The method of claim 1, wherein the ulcer is a Buruli ulcer.

6. The method of claim 1, wherein the hand-held imaging device is a smart device.

7. The method of claim 1, wherein the animal body is a human body.

8. The method of claim 1, wherein performing the simultaneous analyses occurs in real time.

9. A digital processor-implemented method for performing in real time simultaneous analyses of an object on human skin, comprising the processor executable steps of:
imaging the object with a portable smart device;
performing simultaneously on the image of the object an analysis of an object of interest as a skin cancer and an analysis of the object as an ulcer;
classifying the object as a skin cancer or as an ulcer or as neither from results obtained from the skin cancer analysis and the ulcer analysis; and
displaying the results as each result occurs,
wherein the analysis is for a skin cancer, said processor executable steps comprising:

a) obtain luminance and color components of the imaged object;
b) classify pixels comprising the image as object pixels, if they belong to a common luminance and color foreground, as background pixels if they belong to a common luminance and color background or as remaining pixels if they are not classified as foreground pixels or background pixels; and
c) apply a supervised classifier to the remaining pixels to classify them as object or background;
d) calculate a saliency value for a plurality of patches within the segmented object and separate the patches into regions based on the saliency values;
e) calculate an average intensity for the regions to identify them as a higher or as a lower intensity region;
f) determine a sampling percentage for the intensity regions;
g) sample patches within the intensity regions by corresponding sampling percentages;
h) extract one or more feature representations for the object;
i) training a support vector machine (SVM) with known manually segmented objects from a skin cancer; and
j) classifying the object as a skin cancer or not a skin cancer based on the extracted feature representations inputted into the SVM trained with the manually segmented objects from a known skin cancer, and
wherein the analysis is for an ulcer, said processor executable steps comprising:
performing simultaneously steps b) to h) for classifying the skin cancer, on the image obtained in step a), and
wherein the analysis is for an ulcer, said processor executable steps comprising:
performing simultaneously steps b) to h) for classifying the skin cancer, on the image obtained in step a);
i) training a support vector machine (SVM) with known manually segmented objects from an ulcer; and
j) classifying the object as an ulcer or not an ulcer based on the extracted feature representations inputted into the SVM trained with the manually segmented objects from a known ulcer.

10. The method of claim 9, wherein the skin cancer is a melanoma.

11. The method of claim 9, wherein the ulcer is a Buruli ulcer.

12. The method of claim 9, said method further comprising processor executable steps of:
reading input white light image as RGB and the segmentation result of the region;
reading input multispectral images in color channels and transform to gray scale;
registering multispectral images via maximization of mutual information with white light image as reference;
extracting feature representations within the region of interest of multispectral images and within white light images; and
selecting one or more relevant features from a pool of the extracted features.

13. The method of claim 9, said method further comprising processor executable steps of:
reading input white light image as RGB and the segmentation result of the region;
reading input multispectral images in color channels and transform to gray scale;
registering multispectral images via maximization of mutual information with white light image as reference;

determining a volume fraction of melanin (Vmel), a volume fraction of blood (Vblood), and a fraction of blood that is oxygenated (Voxy) for each region of interest ROI pixel to reconstruct maps of melanin, blood and oxygenating percentage;

extracting feature representations within the region of interest from the reconstructed maps; and selecting one or more relevant features from a pool of the extracted features.

* * * * *